(12) United States Patent
Jönsson

(10) Patent No.: US 8,870,804 B2
(45) Date of Patent: Oct. 28, 2014

(54) BLOOD TREATMENT APPARATUS AND METHOD

(75) Inventor: Lennart Jönsson, Bjäred (SE)

(73) Assignee: Gambro Lundia AB, Lund (SE)

( * ) Notice: Subject to any disclaimer, the term of this patent is extended or adjusted under 35 U.S.C. 154(b) by 316 days.

(21) Appl. No.: 12/937,845

(22) PCT Filed: Apr. 14, 2009

(86) PCT No.: PCT/EP2009/054409
§ 371 (c)(1),
(2), (4) Date: Oct. 14, 2010

(87) PCT Pub. No.: WO2009/127627
PCT Pub. Date: Oct. 22, 2009

(65) Prior Publication Data
US 2011/0034850 A1    Feb. 10, 2011

Related U.S. Application Data

(60) Provisional application No. 61/044,927, filed on Apr. 15, 2008.

(30) Foreign Application Priority Data

Apr. 15, 2008 (SE) ...................................... 0800857

(51) Int. Cl.
*A61M 37/00* (2006.01)
*A61M 1/16* (2006.01)
*A61M 1/30* (2006.01)
*A61M 1/10* (2006.01)

(52) U.S. Cl.
CPC . *A61M 1/30* (2013.01); *A61M 1/16* (2013.01); *A61M 1/1005* (2014.02)
USPC ...................................................... 604/4.01

(58) Field of Classification Search
USPC ...................................................... 604/4.01
See application file for complete search history.

(56) References Cited

U.S. PATENT DOCUMENTS 3,883,272 A    5/1975 Puckett
4,209,391 A *  6/1980 Lipps et al. .................... 210/647
(Continued)

FOREIGN PATENT DOCUMENTS

DE    42 40 681 A1    6/1994
EP    0 240 101 A2    10/1987
(Continued)

OTHER PUBLICATIONS

International Search Report from the European Patent Office for International Application No. PCT/EP2009/054409 (Mail date Aug. 26, 2009).

*Primary Examiner* — Susan Su
*Assistant Examiner* — Guy K Townsend
(74) *Attorney, Agent, or Firm* — Nixon & Vanderhye P.C.

(57) ABSTRACT

A proposed blood treatment apparatus includes a blood treatment unit, at least one fluid pump and at least one blood pump. The fluid pumps are configured to pass blood treatment fluid through the blood treatment unit, while the blood pumps are configured to extract untreated blood from a blood source, e.g. a patient, pass the extracted blood through the blood treatment unit and deliver treated blood to a target vessel, e.g. likewise represented by a patient. Each blood pump includes a pumping chamber, which is separated into a first accumulation container and a second accumulation container by a flexible member. The flexible member is further movable within the pumping chamber so as to vary a volume relationship between the first and second accumulation containers. The second accumulation container is configured to receive an amount of blood treatment fluid to act on the flexible member and thus pump blood from the first accumulation container.

26 Claims, 15 Drawing Sheets

(56) References Cited

U.S. PATENT DOCUMENTS

| | | | | |
|---|---|---|---|---|
| 4,267,040 A | * | 5/1981 | Schal | 210/104 |
| 4,366,061 A | * | 12/1982 | Papanek et al. | 210/647 |
| 4,477,342 A | * | 10/1984 | Allan et al. | 210/87 |
| 4,486,189 A | | 12/1984 | Troutner et al. | |
| 4,530,759 A | * | 7/1985 | Schal | 210/104 |
| 4,552,552 A | * | 11/1985 | Polaschegg et al. | 604/6.05 |
| 4,614,590 A | * | 9/1986 | Rath et al. | 210/637 |
| 4,618,343 A | * | 10/1986 | Polaschegg | 604/29 |
| 4,650,457 A | | 3/1987 | Morioka et al. | |
| 4,650,458 A | * | 3/1987 | Dahlberg et al. | 604/6.06 |
| 4,702,829 A | * | 10/1987 | Polaschegg et al. | 210/195.2 |
| 4,708,802 A | * | 11/1987 | Rath et al. | 210/641 |
| 4,711,715 A | * | 12/1987 | Polaschegg | 210/103 |
| 4,715,959 A | * | 12/1987 | Allan et al. | 210/637 |
| 4,770,769 A | * | 9/1988 | Schael | 210/96.2 |
| 4,834,888 A | * | 5/1989 | Polaschegg | 210/646 |
| 4,838,865 A | * | 6/1989 | Flank et al. | 604/118 |
| 4,857,199 A | * | 8/1989 | Cortial | 210/646 |
| 4,971,700 A | * | 11/1990 | Tsuji et al. | 210/647 |
| 5,173,125 A | * | 12/1992 | Felding | 134/22.11 |
| 5,211,849 A | * | 5/1993 | Kitaevich et al. | 604/5.04 |
| 5,542,919 A | * | 8/1996 | Simon et al. | 604/29 |
| 5,660,722 A | | 8/1997 | Nederlof | 210/90 |
| 5,702,597 A | * | 12/1997 | Chevallet et al. | 210/195.2 |
| 5,846,419 A | * | 12/1998 | Nederlof | 210/323.1 |
| 5,910,252 A | * | 6/1999 | Truitt et al. | 210/645 |
| 6,139,748 A | * | 10/2000 | Ericson et al. | 210/646 |
| 6,254,567 B1 | * | 7/2001 | Treu et al. | 604/29 |
| 6,280,632 B1 | * | 8/2001 | Polaschegg | 210/739 |
| 6,491,656 B1 | * | 12/2002 | Morris | 604/6.09 |
| 6,572,576 B2 | * | 6/2003 | Brugger et al. | 604/4.01 |
| 6,579,494 B1 | * | 6/2003 | Chevallet et al. | 422/3 |
| 6,582,385 B2 | * | 6/2003 | Burbank et al. | 604/5.04 |
| 6,638,478 B1 | * | 10/2003 | Treu et al. | 422/44 |
| 6,645,166 B2 | | 11/2003 | Scheunert et al. | |
| 6,852,090 B2 | * | 2/2005 | Burbank et al. | 604/6.11 |
| 6,899,693 B2 | | 5/2005 | Ghelli et al. | |
| 6,979,309 B2 | * | 12/2005 | Burbank et al. | 604/6.16 |
| 2002/0147423 A1 | * | 10/2002 | Burbank et al. | 604/6.16 |
| 2004/0243046 A1 | * | 12/2004 | Brugger et al. | 604/4.01 |
| 2004/0243047 A1 | * | 12/2004 | Brugger et al. | 604/4.01 |
| 2004/0243050 A1 | * | 12/2004 | Treu et al. | 604/4.01 |
| 2004/0249331 A1 | * | 12/2004 | Burbank et al. | 604/4.01 |
| 2004/0267184 A1 | * | 12/2004 | Burbank et al. | 604/6.11 |
| 2005/0011823 A1 | * | 1/2005 | Delnevo et al. | 210/252 |
| 2005/0011833 A1 | * | 1/2005 | Stahl | 210/646 |
| 2005/0131332 A1 | * | 6/2005 | Kelly et al. | 604/4.01 |
| 2011/0024353 A1 | * | 2/2011 | Jonsson et al. | 210/637 |
| 2011/0034850 A1 | * | 2/2011 | Jonsson | 604/4.01 |
| 2011/0046535 A1 | * | 2/2011 | Jonsson et al. | 604/6.11 |
| 2011/0201988 A1 | * | 8/2011 | Holmer et al. | 604/6.09 |
| 2011/0201989 A1 | * | 8/2011 | Holmer et al. | 604/6.11 |

FOREIGN PATENT DOCUMENTS

| | | |
|---|---|---|
| EP | 1 652 541 A1 | 5/2006 |
| WO | WO 03/070314 A1 | 8/2003 |
| WO | WO 2005/092408 A1 | 10/2005 |

\* cited by examiner

BLOOD TREATMENT APPARATUS AND METHOD

CROSS REFERENCE TO RELATED APPLICATIONS

This application is a national phase application based on PCT/EP2009/054409 filed Apr. 14, 2009, which claims the benefit of Swedish Patent Application No. SE 0800587-5, filed Apr. 15, 2008, and U.S. Provisional Application No. 61/044,927, filed Apr. 15, 2008, the contents of all of which are incorporated herein by reference.

THE BACKGROUND OF THE INVENTION AND PRIOR ART

The present invention relates generally to extracorporeal blood treatment. More particularly the invention relates to a blood treatment apparatus according to the preamble of claim 1 and a method according to the preamble of claim 12. The invention also relates to a computer program according to claim 23 and a computer readable medium according to claim 24.

A conventional single-needle blood treatment apparatus, for instance a hemodialysis system or a hemodiafiltration system, contains a dialysis fluid circuit and a blood circuit with one or two blood pumps. For patient security reasons, single-needle dialysis is advantageous in a self care setting. Namely, here, there is no risk for dislodgement of a venous needle and thereby loss of blood being pumped out unintentionally via an arterial needle. Additionally, fewer needle punctures to the patient blood access are required relative to dual-needle treatment. Generally, the single-needle system is also well suited for long lasting treatments, such as nocturnal treatments. Moreover, single-needle dialysis may be used when the patient blood access is defective.

The prior art includes a range of examples of solutions for single-needle blood treatment, as well as pump means adapted to such implementations. For example, U.S. Pat. No. 4,552,552 describes a dialysis pumping system for a single-needle dialysis apparatus with a dialyzer having blood and dialysate circuits, and wherein the blood inlets and outlets are joined by intake and outtake lines with at least one blood connection. The intake line has a driving pump and pump valves placed upstream and downstream of the blood pump. The blood pump unit has a generally stiff housing with a diaphragm therein walling off the space in the housing into a first chamber for blood and a second chamber for driving fluid that is joined up with the driving pump. A respective high and low pressure limiting valve means prevent pressure levels outside a given interval by venting the working chamber whenever the pressure falls outside predetermined threshold values.

U.S. Pat. No. 6,645,166 reveals a blood treatment device and disposable kit for a blood treatment device, e.g. a dialysis machine, which permits both single- and dual-needle operation. Here, a blood treatment unit has an inlet connected to a feed line and an outlet connected to a return line. The feed line has two parallel line branches, where a positive displacement pump is connected to a first line branch, and a negative displacement pump is connected to a second line branch. Moreover, a connection line is provided to produce a fluid connection between the outlet of the blood treatment unit and one of the two pumps. For single-needle operation, the feed and return lines are brought together and connected to a common needle.

U.S. Pat. No. 6,899,693 discloses a compact pulsating pumping unit including means suitable to draw blood from an intake connector in order to send it to an outlet connector. Said means are contained in an enclosure provided with valves connected to the inlet and the outlet. An elastic membrane here separates the enclosure into two domes. This allows a working fluid to act on one side of the membrane, such that the membrane acts on blood located on the opposite side. The membrane thereby controls the operation of an inlet valve and an outlet valve, such that blood is moved into respective out from a pumping chamber.

Although the above solutions may have specific beneficial characteristics, they fail to provide an overall optimal fluid flow in a blood treatment apparatus. Moreover, operating the apparatus requires pressure measurements on the blood side. Hence, the design of the apparatus is compelled to be relatively intricate, and handling the apparatus becomes impractical. This, in turn, renders the apparatus unsuitable for a self care setting. Furthermore, blood pressure measurements on the blood side are problematic due to the potential risk of infection and contamination of the blood via the pressure measuring means. Specifically, in a self care setting, the patient risks to be stricken with infections caused by his/her own blood residuals from earlier treatments, whereas in a hospital environment infectious substances may be transferred from one patient to another.

SUMMARY OF THE INVENTION

The object of the present invention is therefore to alleviate the above problems and provide an uncomplicated blood treatment solution which is efficient with respect to the overall fluid flow and well adapted for a home/self care environment.

According to the invention, the object is achieved by the apparatus as initially described, wherein the at least one fluid pump and the at least one blood pump are arranged such that the blood treatment fluid constitutes the working fluid for the at least one blood pump.

The proposed blood treatment apparatus is advantageous because the design is very reliable and cost efficient. Furthermore, the liquid coupling between the blood and the blood treatment fluid via the flexible member of the pumping chamber renders it possible to measure the blood pressure in the apparatus by studying the pressure of the blood treatment fluid. This, in turn, enhances both the patient safety and the user friendliness. Additionally, since no blood pressure measuring means are required on the blood side, servicing the apparatus is facilitated and the risk of infection/contamination of the blood is reduced. The risk for blood leakage is reduced.

According to one embodiment of the invention, the apparatus includes at least one pressure measuring means configured to register a first pressure parameter representing a first pressure level of the untreated blood extracted from the blood source and a second pressure parameter representing a second pressure level of the treated blood delivered to the target vessel. Here, each of the at least one pressure measuring means is arranged on a fluid conduit configured to transport the blood treatment fluid. Hence, the pressure of the blood leaving the blood source (e.g. represented by a patient) and the pressure of the blood being delivered to the target vessel (e.g. represented by the patient from whom blood was extracted) can be registered in a very simple and straightforward manner, which is also clinically safe.

According to an alternative embodiment of the invention a pressure measuring device is arranged on a blood fluid conduit configured to transport the blood.

According to another embodiment of the invention, the apparatus includes a first blood valve means configured to control the extraction of untreated blood from the blood source. The apparatus further includes a second blood valve means configured to control the delivery of treated blood to the target vessel. Hence, by opening and closing the first and second blood valve means in an alternating manner, untreated blood may be extracted from the blood source and treated blood may be delivered to the target vessel according to a cyclic process.

According to a further embodiment of the invention, the apparatus includes a fluid inlet conduit configured to receive fresh blood treatment fluid into the apparatus, and a fluid outlet conduit configured to discharge used blood treatment fluid from the apparatus. Thereby, for example a flow of dialysis fluid and dialysate through the apparatus can be conveniently effected.

According to yet another embodiment of the invention, the apparatus includes a single blood pump, a fluid valve means and a control unit. The fluid valve means is here arranged to direct a flow of blood treatment fluid in respect of the blood pump. This means that the fluid valve means directs fresh fluid from the pump through the blood treatment unit during a first phase, and charges the pump with fresh fluid during a second phase; or charges the pump with used fluid during the first phase, and directs fresh fluid through the blood treatment unit during the second phase. The apparatus further includes a control unit, which is configured to control the fluid valve means to open and close repeatedly. Hence, the apparatus may be controlled so that the blood treatment unit either receives intermittent simultaneous flows of blood and blood treatment fluid; or receives alternating flows of blood and blood treatment fluid.

The fluid valve means is either arranged on a fluid inlet for feeding fresh blood treatment fluid through the blood treatment unit, or on the fluid outlet for discharging used blood treatment fluid from the apparatus. In both cases the control unit realizes a cyclic process.

In the former case, the control unit is configured to control the fluid valve means to: direct a flow of fresh blood treatment fluid from the second accumulation container of the blood pump to the blood treatment unit during a first phase of the cyclic process; and direct a flow of fresh blood treatment fluid from the fluid container to the second accumulation container during a second phase of the cyclic process.

In the latter case, however, the control unit is configured to control the fluid valve means to: direct a flow of used blood treatment fluid from the second accumulation container of the blood pump out through the discharge outlet during the first phase of the cyclic process; and direct a flow of used blood treatment fluid from the blood treatment unit into the second accumulation container during a second phase of the cyclic process.

According to still another embodiment of the invention, the apparatus includes a first blood pump and a second blood pump. The first blood pump is configured to receive untreated blood from the blood source into its first accumulation container, and discharge used blood treatment fluid from its second accumulation container during a first phase of a cyclic process. During a second phase of the cyclic process, the first blood pump is configured to receive fresh blood treatment fluid from the blood treatment unit in its second accumulation container and eject untreated blood from its first accumulation container into the blood treatment unit. The second blood pump is configured to eject fresh blood treatment fluid into the blood treatment unit from its second accumulation container, and receive treated blood from the blood treatment unit in its first accumulation container during the first phase of the cyclic process. During the second phase of the cyclic process, the second blood pump is configured to eject treated blood from its first accumulation container to the target vessel, and receive fresh blood treatment fluid in its second accumulation container. This design is advantageous, since it enables non-stop flows of blood and blood treatment fluid through the blood treatment unit.

According to a further embodiment of the invention, the apparatus includes first and second fluid pumps. The first fluid pump is arranged on the fluid inlet conduit, and this pump is configured to feed fresh blood treatment fluid into the apparatus. The second fluid pump is arranged on the fluid outlet conduit, and this pump is configured to discharge used blood treatment fluid from the apparatus. Optionally, the control unit, in turn, is configured to control the operation of the first and second fluid pumps in response to the first and second pressure parameters, such that desired transitions between the above-mentioned first and second phases of the cyclic process are attained.

According to still a further embodiment of the invention at least one of the blood pumps is provided with an inlet for blood treatment fluid that is separate from the outlet of blood treatment fluid.

According to another aspect of the invention the object is achieved by the method described initially, wherein in a first phase, blood is received in the first accumulation container, and blood treatment fluid is ejected from the second accumulation container. Here, either fresh fluid is fed to the blood treatment unit, or used fluid is being discharged for discarding. In a second phase subsequent to the first phase, the first accumulation container is configured to eject blood to the target vessel. Depending on the apparatus design, this may involve feeding untreated blood through the blood treatment unit for further delivery to the target vessel, or feeding already treated blood back to the target vessel. Additionally, during the second phase, blood treatment fluid is received in the second accumulation container (i.e. either fresh fluid, or used fluid, depending on the specific design of the apparatus).

The advantages of this method, as well as the embodiments thereof, are apparent from the discussion above with reference to the proposed apparatus.

According to a further aspect of the invention the object is achieved by a computer program, which is directly loadable into the memory of a computer, and includes software adapted to control the method proposed above when said program is run on a computer.

According to another aspect of the invention the object is achieved by a computer readable medium, having a program recorded thereon, where the program is to control a computer to perform the method proposed above when the program is loaded into the computer.

Although the invention is applicable to dual-needle implementations, it is especially advantageous for blood treatment in the form of single-needle hemodialysis or hemodiafiltration. The solution is particularly suitable for self care treatment, daily/nocturnal dialysis and intensive care. Further advantages, beneficial features and applications of the present invention will be apparent from the following description and the dependent claims.

BRIEF DESCRIPTION OF THE DRAWINGS

The present invention is now to be explained more closely by means of embodiments, which are disclosed as examples, and with reference to the attached drawings.

DESCRIPTION OF EMBODIMENTS OF THE INVENTION

Figure 1A:
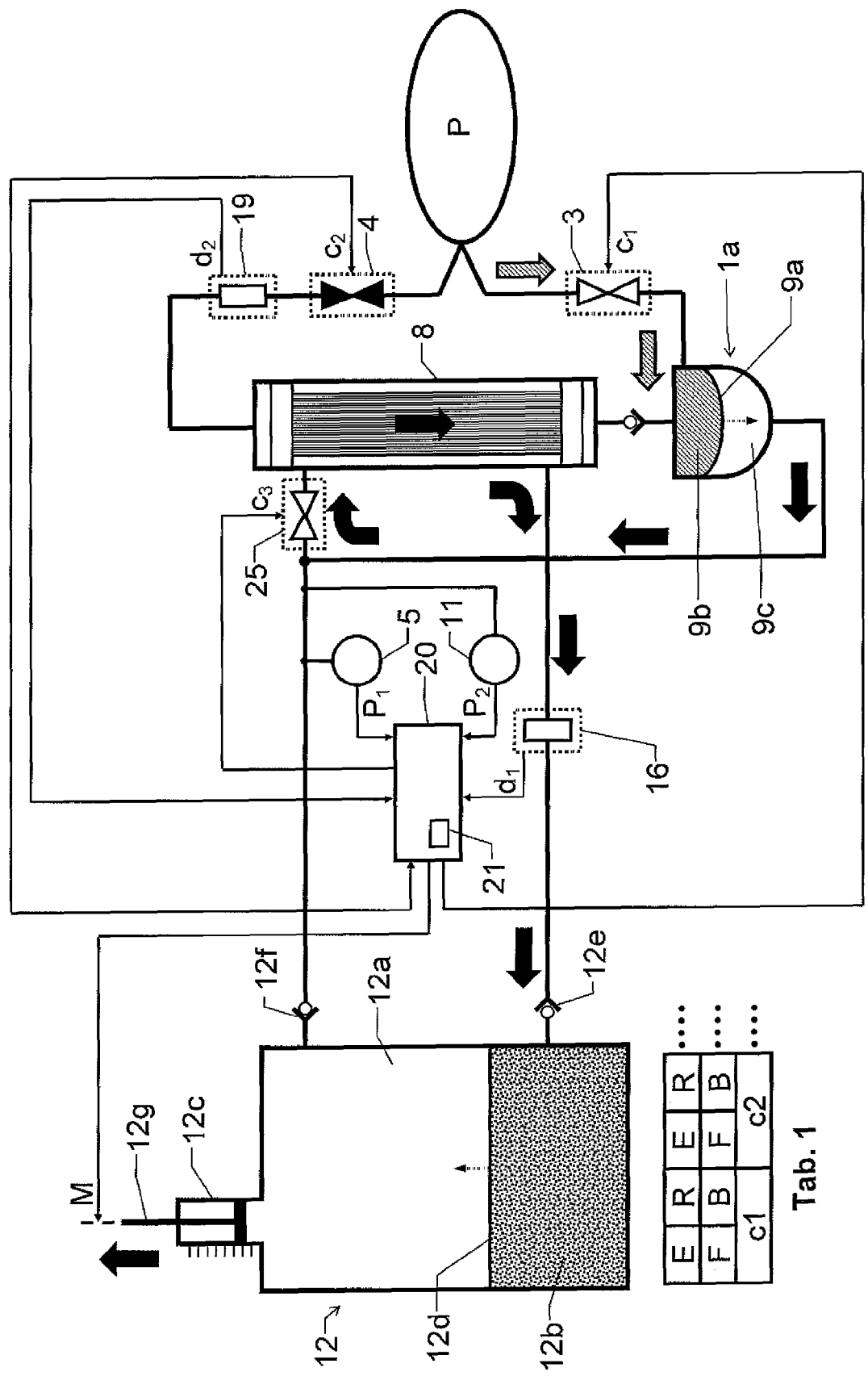
FIG. 1a shows a block diagram over a blood treatment apparatus according to a first embodiment of the invention during a first phase of a cyclic treatment process.

We refer initially to FIG. 1a, which shows a block diagram over a blood treatment apparatus (e.g. a dialysis apparatus) according to a first embodiment of the invention during a first phase of a cyclic process.

The apparatus includes a blood treatment unit 8 (typically represented by a dialyzer), a reciprocal fluid pump 12c and a blood pump 1a. The fluid pump 12c is configured to pass a blood treatment fluid (e.g. dialysis fluid) from a reservoir compartment 12a of a rigid fluid container 12 through the blood treatment unit 8, however via the blood pump 1a. The blood pump 1a is further configured to extract untreated blood from a blood source, here a patient P; pass the extracted blood through the blood treatment unit 8 and deliver treated blood to a target vessel, here represented by the patient P.

The blood pump 1a has a pumping chamber, which is separated into first and second accumulation containers 9b and 9c respectively by a flexible member 9a, e.g. in the form of a soft/elastic membrane. The flexible member 9a is movable within the pumping chamber so as to vary a volume relationship between the first and second accumulation containers 9b and 9c. Further, the first accumulation container 9b is configured to receive an amount of untreated blood from the patient P, and the second accumulation container 9c is configured to receive an amount of fresh blood treatment fluid from the fluid container 12. Hence, the blood treatment fluid may act on the blood with the flexible member 9a as a separating interface. Consequently, the blood treatment fluid can be used to pump the blood, i.e. extract blood from the patient P, pass the extracted blood through the blood treatment unit 8, and return treated blood to the patient P.

To allow the blood treatment apparatus to operate in a desired manner, the apparatus includes first and second blood valve means 3 and 4 respectively. The first blood valve means 3 is configured to control the extraction of untreated blood from the patient P via a needle, and the second blood valve means 4 is configured to control the return of treated blood to the patient P, likewise via a needle. The blood valve means 3 and 4 need to be activated alternately, such that the first blood valve means 3 is open while the second blood valve 4 is closed, and vice versa.

Figure 1B:
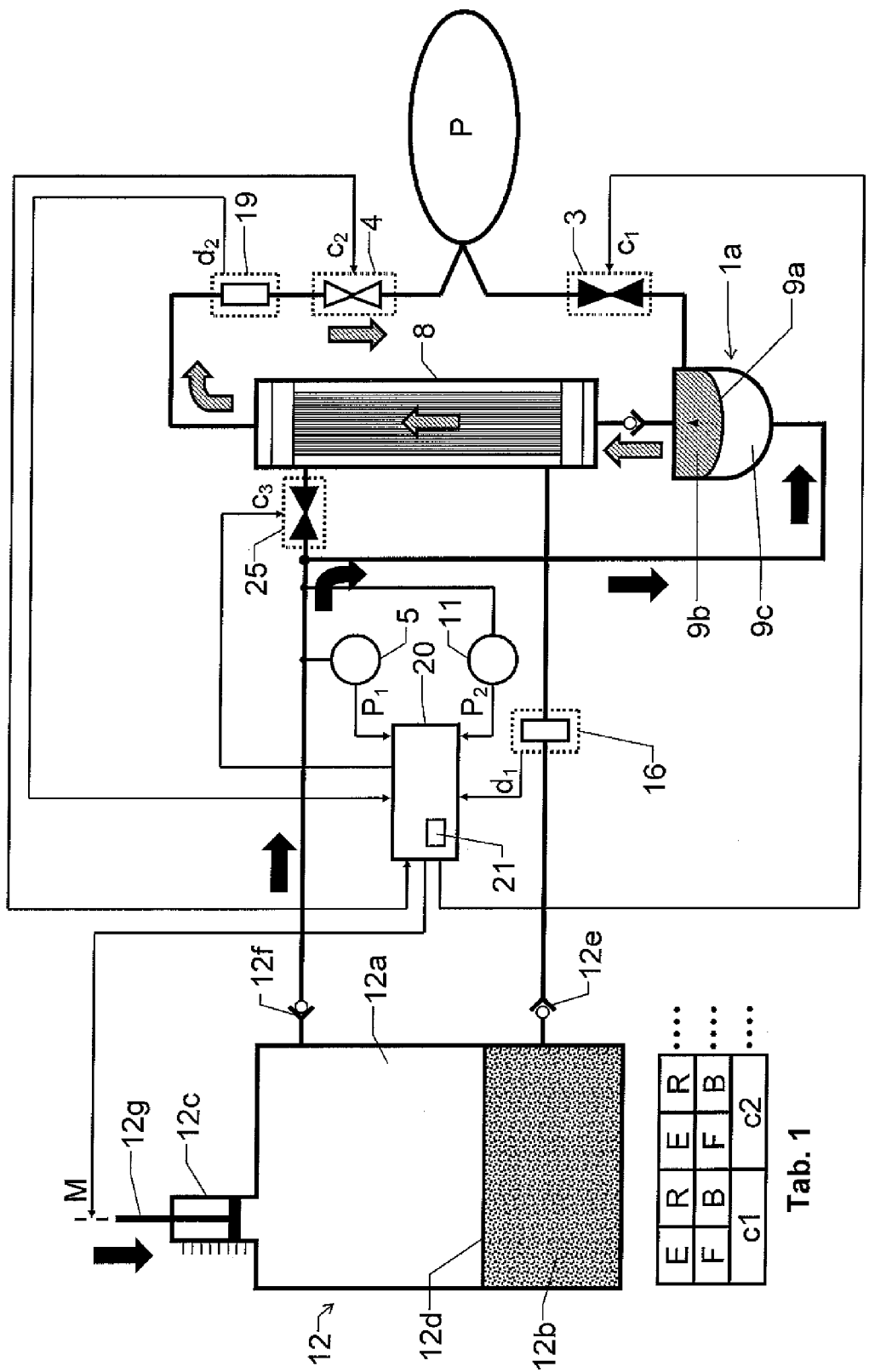
FIG. 1b shows the block diagram over the blood treatment apparatus according to the first embodiment of the invention during a second phase of the cyclic process.

Moreover, the blood pump 1a and the fluid pump 12c are controlled according to a cyclic process, wherein the operation cycles of the fluid pump 12c and the blood pump 1a are synchronized. This means that, during a first phase the blood pump 1 receives blood contemporaneous with the fluid pump 12c performing a first pump action. Here, this means moving a piston element 12g outwards, thereby moving a division wall 12d, such that an under pressure is created. This, in turn, causes a suction force acting on the blood pump 1a to pump fresh blood treatment fluid out from the second accumulation container 9c. During a second phase (illustrated in FIG. 1b), subsequent to the above-mentioned first phase, the fluid pump 12c performs a second pump action. Here, this means moving the piston element 12g inwards. The division wall 12d is locked in its present position, which causes fresh blood treatment fluid to be pushed into the second accumulation container 9c. This, in turn, results in that the blood pump 1a ejects untreated blood into the blood treatment unit 8. The fresh blood treatment fluid leaves the fluid container 12 via a non-return valve 12f.

To achieve this function, the first and second blood valve means 3 and 4 are controlled in coordination with the operation of the fluid pump 12c. Furthermore, in course of the process (i.e. extracting untreated blood from the blood source/patient P and delivering treated blood to the target vessel/patient P), it is desirable that the blood pressure be monitored. To this aim, it is preferable if the blood treatment apparatus includes at least one pressure measuring means. In the embodiment of the invention illustrated in FIGS. 1a and 1b, pressure measuring means are included in the form of 5 and 11 respectively. A first blood pressure measuring means 5 is configured to register a first pressure parameter $P_1$ representing a first pressure level of the untreated blood extracted from the patient P, and a second blood pressure measuring means 11 is configured to register a second pressure parameter $P_2$ representing a second pressure level of the treated blood being returned to the patient P. I.e. the second pressure parameter $P_2$ is measured over the blood treatment unit 8. According to this embodiment of the invention, both the pressure measuring means 5 and 11 are arranged on a fluid conduit configured to transport fresh blood treatment fluid from the fluid container 12a. Consequently, neither of these units come into contact with the blood. Instead, the blood pressure is measured via the blood treatment fluid, which due to the contact with the flexible member 9a has a pressure level equal to that of the blood. Additionally, since, as will be further elucidated below, the first and second pressure parameters $P_1$ and $P_2$ are registered at different points in time, a single pressure measuring means is actually sufficient to determine both parameters $P_1$ and $P_2$.

As already mentioned, FIG. 1a illustrates a first phase of a cyclic process during which untreated blood is extracted from the patient P. To this aim, the first blood valve means 3 is open and the second blood valve 4 is closed. The fluid pump 12c also performs a pump action wherein its piston element 12g moves outwards. As a result, fresh blood treatment fluid is sucked out from the second accumulation container 9c, and the blood volume in the first accumulation container 9b increases. Therefore, the first phase may also be referred to as the blood extraction phase, denoted E in Table 1. Analogously, the second phase illustrated in FIG. 1b may be referred to as the blood return phase, denoted R in Table 1. Here, the first and second phases complete a first cycle c1 of the process. Then follows a second cycle c2, and so on. Table 1 also shows a symbol F denoting that blood treatment fluid is passed through the blood treatment unit 8, and a symbol B denoting that blood is passed through the blood treatment unit 8. As can be seen, in this embodiment, the blood treatment fluid and the blood pass through the blood treatment unit 8 in the form of alternating flows, i.e. one separate flow in each respective phase E or R.

The used blood treatment fluid is discharged from the second accumulation container 9c via a first working fluid port into a fluid outlet conduit. After leaving the blood pump 1a, the blood treatment fluid passes through a semi permeable membrane of the blood treatment unit 8, and continues into a waste compartment 12b of the fluid container 12 via a non-return valve 12e. Optionally, a movable wall member 12d in the fluid container 12 separates the waste compartment 12b from the reservoir compartment 12a in such a manner that the volume of the waste compartment 12b may be gradually increased to accept a growing amount of used blood treatment fluid, and the volume of the reservoir compartment 12a may be decreased correspondingly as the fresh blood treatment fluid is consumed.

Specifically, during the first phase (the blood extraction phase E), the first blood valve means 3 is open, the second blood valve 4 is closed and the fluid valve means 25 is open. The fluid pump 12c also operates to suck fresh blood treatment fluid from the second accumulation container 9c, via the fluid valve means 25, through the blood treatment unit 8, and out from the apparatus. The decrease of the fluid amount in the blood pump 1a, in turn, draws blood from the patient P into the first accumulation container 9b. During the second phase (the blood return phase R), the first blood valve means 3 is closed, the second blood valve 4 is open and the fluid valve means 25 is closed. Additionally, the fluid pump 12c operates to pump fresh blood treatment fluid from the fluid container 12a into the second accumulation container 9c. The increasing amount of the fluid in the blood pump 1a causes the flexible member 9a to push the blood in the first accumulation container 9b through the blood treatment unit 8 and back into the patient P. When passing through the blood treatment unit 8 the blood is treated/cleaned. The amount of blood passing through the blood treatment unit 8 during one cycle is referred to as a stroke volume, i.e. the volume of blood taken from the patient P and brought back to the patient P during one cycle c1, c2 etc.

The blood treatment unit 8 has a fluid outlet conduit, which is configured to discharge used blood treatment fluid from the apparatus during the first phase of the cyclic process. The thus discharged fluid optionally continues into the waste compartment 12b, or down the drain.

It is further advantageous if the apparatus includes a control unit 20, which is configured to receive the above-mentioned first and second pressure parameters $P_1$ and $P_2$. In response to these parameters, the control unit 20 controls the first and second blood valve means 3 and 4 respectively and the fluid valve means 25, such that the cyclic process is effected. Of course, this control also involves controlling the fluid pump 12c. Specifically, during the first phase (the blood extraction phase E), the control unit 20 is configured to generate a first control signal $c_1$ such that the first blood valve means 3 is opened, a second control signal $c_2$ such that the second blood valve means 4 is closed, and a third control signal $c_3$ such that the fluid valve means 25 is opened. Then, during the second phase (the blood return phase R), the control unit 20 is configured to generate the first control signal $c_1$ such that the first blood valve means 3 is closed, the second control signal $c_2$ such that the second blood valve means 4 is opened, and a third control signal $c_3$ such that the fluid valve means 25 is closed. Here, the control unit 20 uses the first and second pressure parameters $P_1$ and $P_2$ to determine appropriate transitions between the first and second phases, and thus controlling the valve means 3, 4 and 25 and the operation of the fluid pump 12c as described above. Particularly, the control unit 20 may control the operation of the fluid pump 12c via a motoric signal M.

Optionally, the control unit 20, in turn, includes, or is associated with; a memory means 21 storing computer software for controlling the control unit 20 to effect the above-described procedure.

It is preferable if a blood leak detector 16 is arranged on the fluid conduit between the blood treatment unit 8 and the non-return valve 12e to the waste compartment 12b. Namely, thereby any malfunction of the apparatus resulting in that blood enters into the fluid path (e.g. due to a leaking blood pump or leakage in the unit 8) may be reported to the control unit 20 via a first detection signal $d_1$. In response to the first detection signal $d_1$, the control unit 20 advantageously generates an alarm, such that appropriate corrective actions can be taken.

Furthermore, the blood fluid circuit optionally includes an air bubble detector 19 and a related air removal device (not shown) being arranged between the blood treatment unit 8 and the second blood valve means 4. If the air removal device fails to eliminate any detected air bubbles, a second detection signal $d_2$ is optionally sent to the control unit 20. In response to this signal $d_2$, the control unit 20 produces an alarm, such that appropriate corrective actions can be taken. Optionally, this involves stopping the apparatus.

Optionally such an air bubble detector 19 and related air removal device is also arranged between the first blood valve means 3 and the first blood pump 1a.

In a start up phase (i.e. prior to initiating the above-mentioned cyclic process) the fluid circuit may be filled (or more precisely filled such that superfluous fluid rinses the circuit) with fresh blood treatment fluid (e.g. dialysis fluid) from the fluid container 12a. The filling of the fluid causes any air in the dialysis fluid circuit to be pushed back into the waste compartment 12b (or drain) where it is vented. Correspondingly, the of the blood circuit may be connected to a saline solution (or other appropriate fluid) to fill and rinse, and thus eliminate any gas bubbles in the blood circuit. This process of filling and rinsing the apparatus is normally referred to as priming.

Figure 2A:
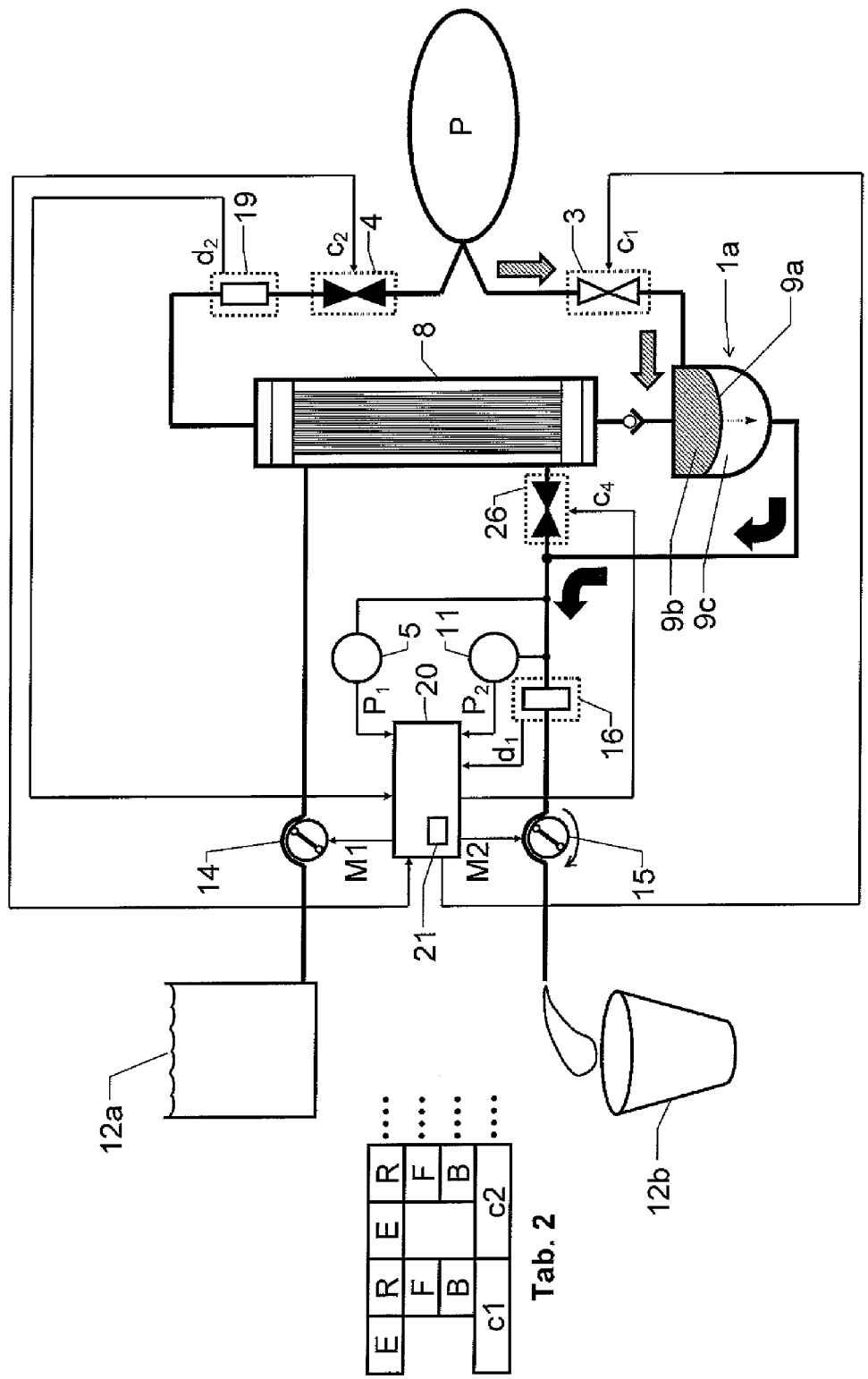
FIGS. 2a-b show block diagrams over a blood treatment apparatus according to a second embodiment of the invention during a first and a second phase respectively of a cyclic treatment process.

FIG. 2a shows a block diagram over a blood treatment apparatus according to a second embodiment of the invention. All units and components having reference signs which also occur in FIGS. 1a and 1b designate the same units and components as those described above with reference to FIGS. 1a and 1b.

The second embodiment differs from the first embodiment of the invention in that the pressure measuring means 5 and 11 are arranged in a fluid conduit configured to transport used blood treatment fluid from the blood treatment unit 8, and a fluid valve means 26 controlled in response to a fourth control $c_4$ is arranged on the fluid conduit from the blood treatment unit 8. A result of this design is that intermittent, however simultaneous flows of blood and blood treatment fluid through the blood treatment unit 8 may be accomplished, as illustrated in Table 2.

Moreover, first and second fluid pumps 14 and 15 respectively replace the reciprocal fluid 12c. First and second motoric signals M1 and M2 from the control unit 20 control the operation of the fluid pumps 14 and 15 respectively.

Figure 2B:
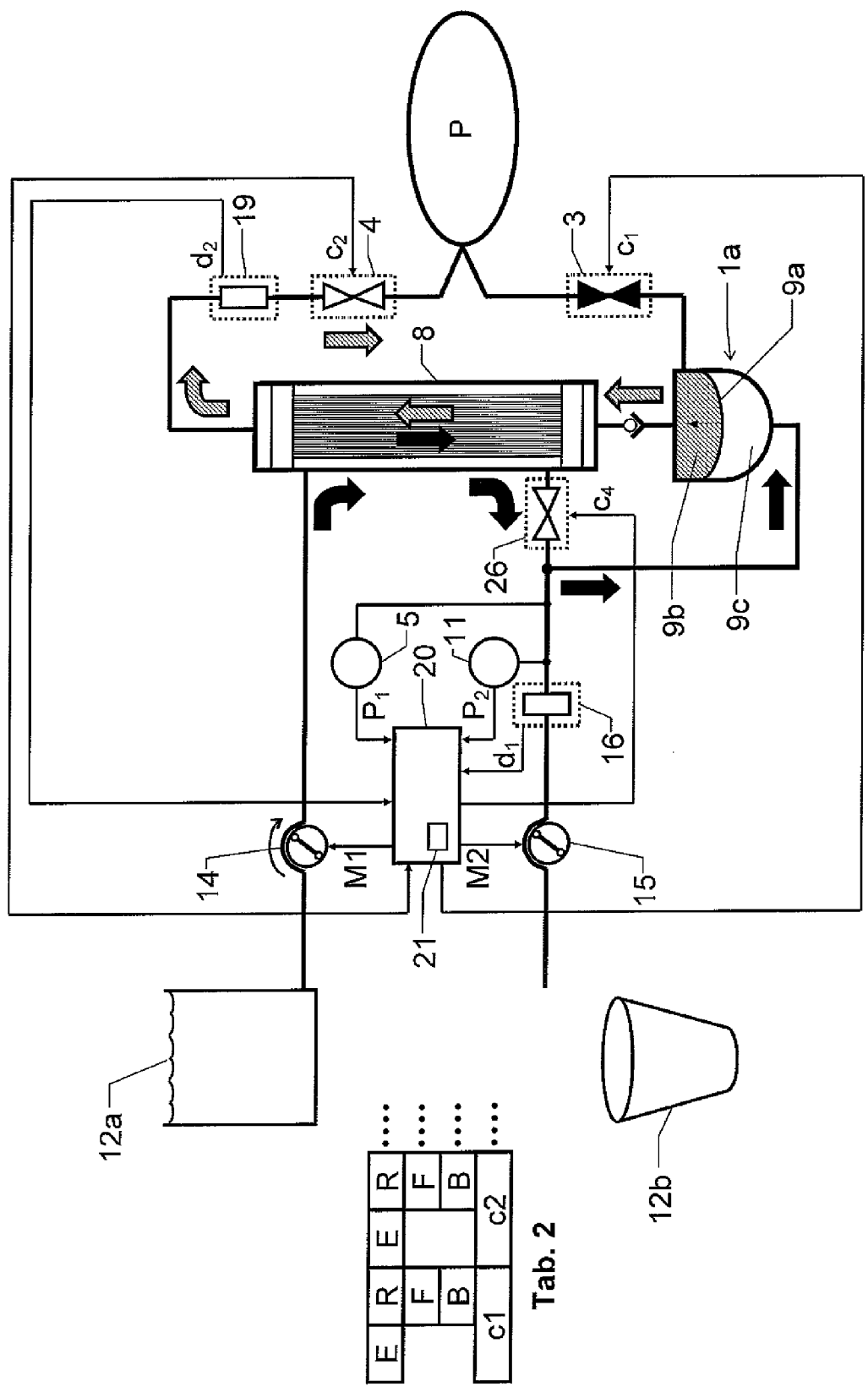

Specifically, during a first phase (the blood extraction phase E), the first accumulation chamber 9b of the blood pump 1a is charged with untreated blood from the patient P. To this aim, used blood treatment fluid is discharged by means of the second fluid pump 15. Then, during a second phase (the blood return phase R), (see FIG. 2b), the first fluid pump 14 pumps fresh blood treatment fluid from the fluid container 12a, through the blood treatment unit 8 and into the second accumulation container 9c of the blood pump 1a. In parallel therewith, blood is pushed through the blood treatment unit 8 and back to the patient P. Hence, blood and blood treatment fluid pass simultaneously through the unit 8.

Figure 2C:
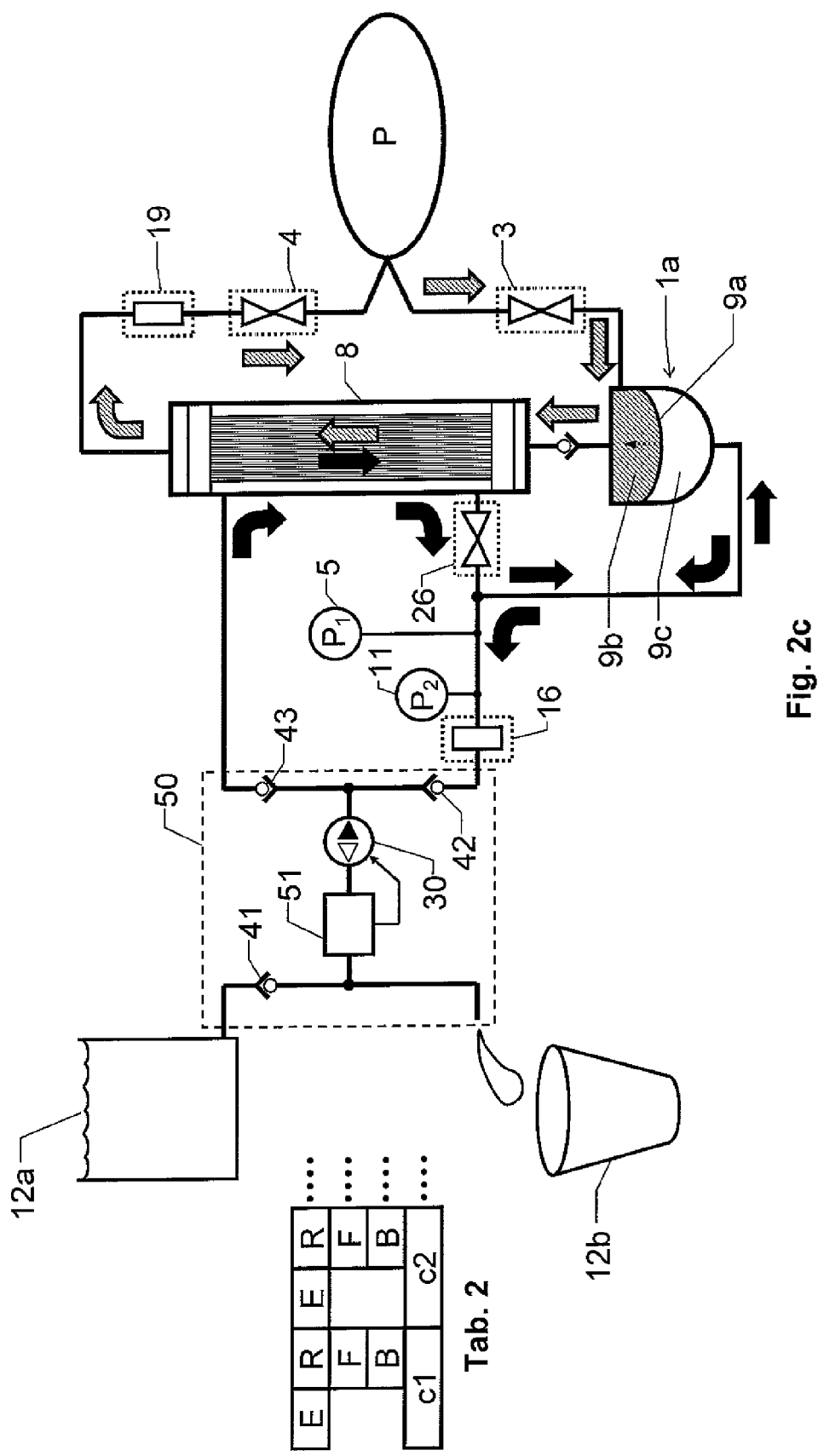
FIG. 2c shows a block diagram over a blood treatment apparatus according to the second embodiment of the invention, which is designed to render a large number of elements in the apparatus disposable.

FIG. 2c shows another block diagram over a blood treatment apparatus according to the second embodiment of the invention. However, the design is here specifically adapted to render a large number of elements in the apparatus disposable. Thereby, for example self care treatment is facilitated. In fact, all units outside the dashed box 50 may be made disposable. Moreover, for clarity reasons, neither the control unit 20 nor the signals to/from this unit are represented in FIG. 2c.

Nevertheless a flow measurement unit 51 and a reversible pump 30 are included. The reversible pump 30 is configured to perform the tasks of the first and second fluid pumps 14 and 15, and the flow measurement unit 51 is configured to accomplish a desired flow of blood treatment fluid through the apparatus. The reversible pump 30 thereby also influences the blood pump 1a to cause blood to be extracted from a blood source/patient P and be delivered to a target vessel/the patient P. Furthermore, a first non-return valves 41 connects the flow measurement unit 51 to the fluid container 12a, a second non-return valve 42 connects the fluid outlet conduit to the reversible pump 30, and a third non-return valve 43 connects the reversible pump 30 to the fluid inlet conduit.

Figure 3A:
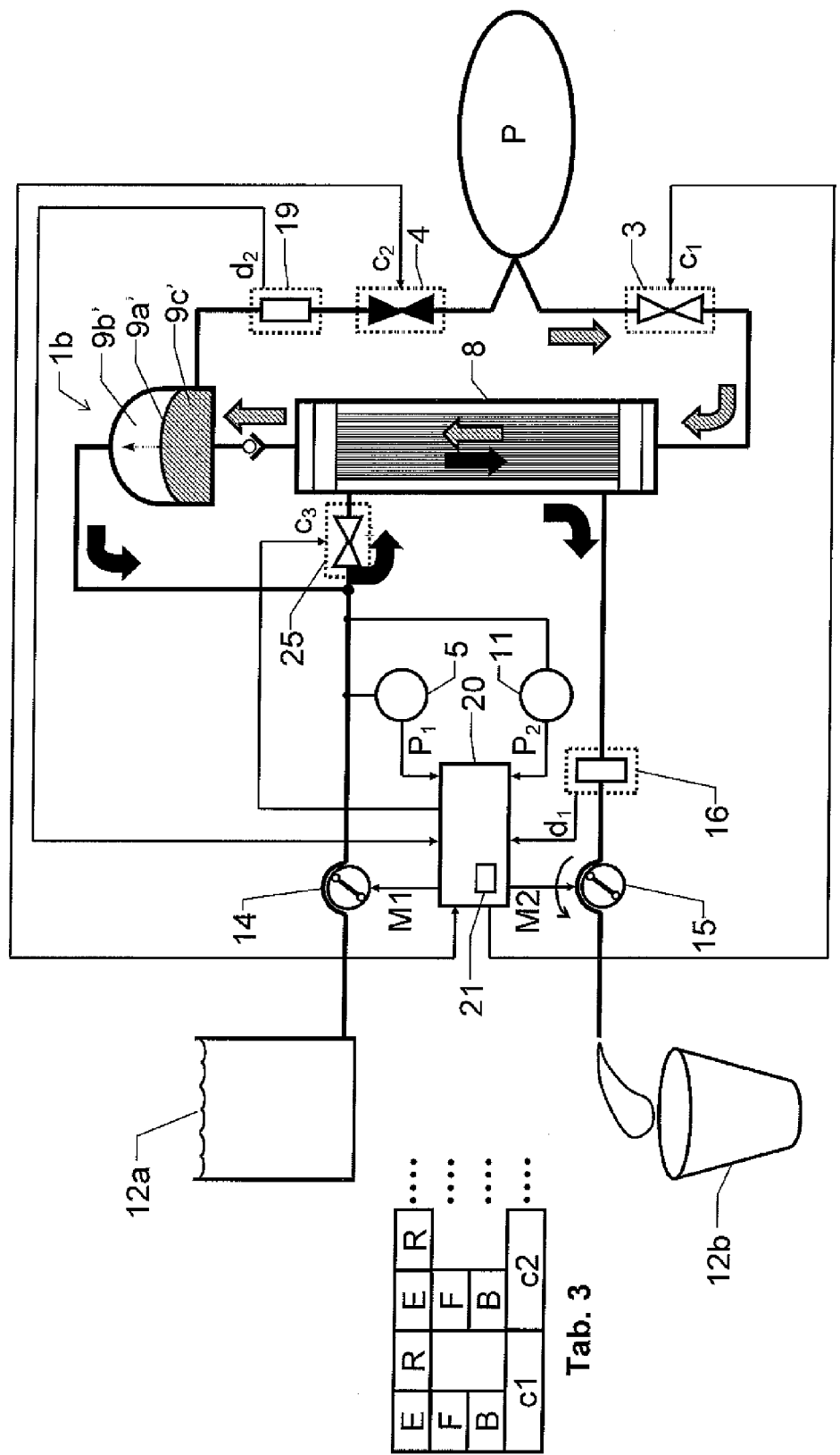
FIGS. 3a-b show block diagrams over a blood treatment apparatus according to a third embodiment of the invention during a first and a second phase respectively of a cyclic treatment process.
Figure 3B:
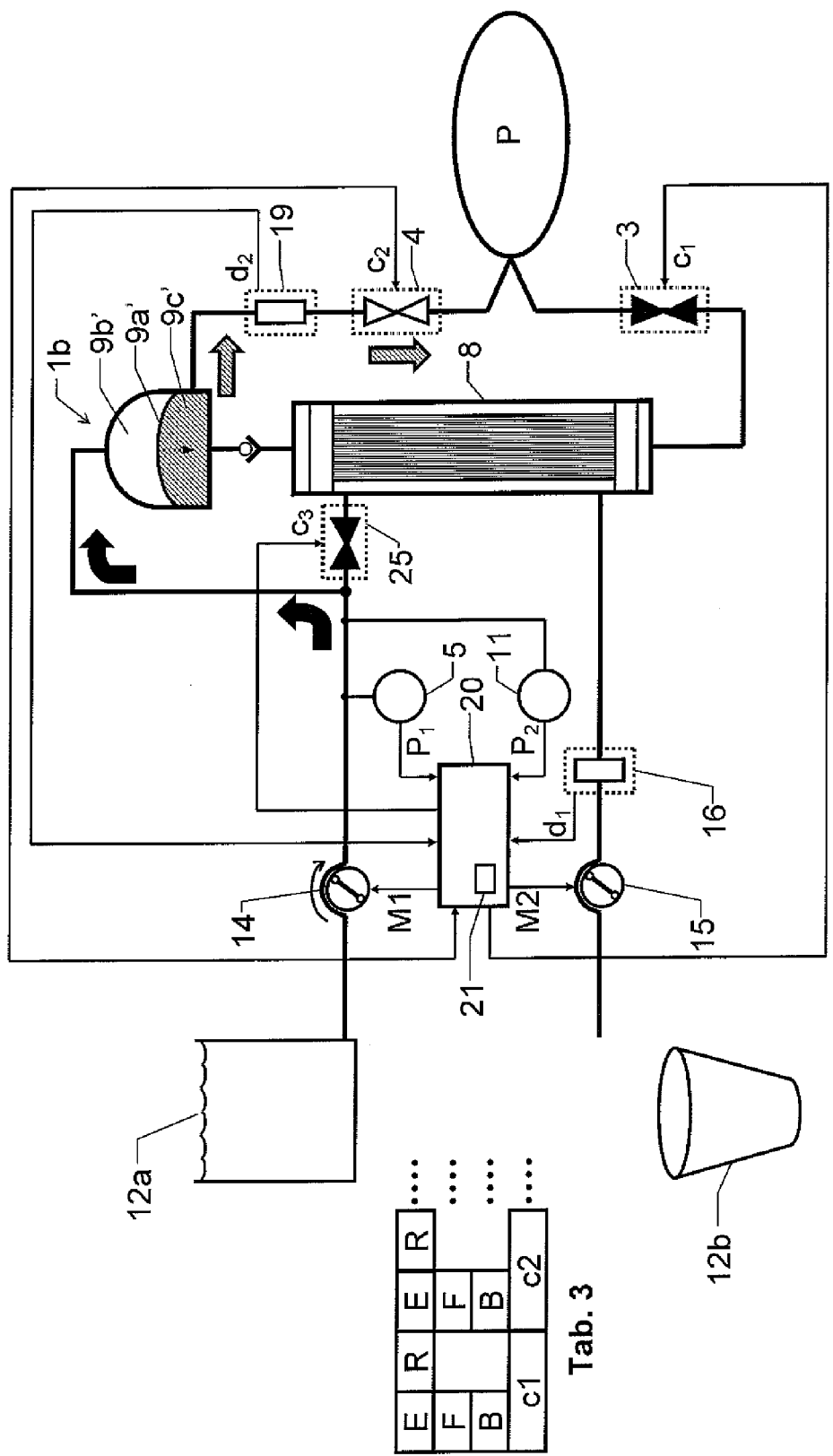

FIG. 3a shows a block diagram over a blood treatment apparatus according to a third embodiment of the invention. All units and components having reference signs which also occur in FIGS. 1a through 2c designate the same units and components as those described above with reference to these Figures.

The third embodiment differs from the first embodiment of the invention in that a blood pump 1b is arranged on the blood outlet from the blood treatment unit 8 (instead of on the blood inlet). A result of this design is that, analogous to the second embodiment, intermittent, however simultaneous flows of blood and blood treatment fluid through the blood treatment unit 8 may be accomplished, as illustrated in Table 3. Consequently, the operation of the apparatus is equivalent to that of the second embodiment; however the blood pump 1b is instead charged with fresh blood treatment fluid during the second phase (the blood return phase R).

Figure 4A:
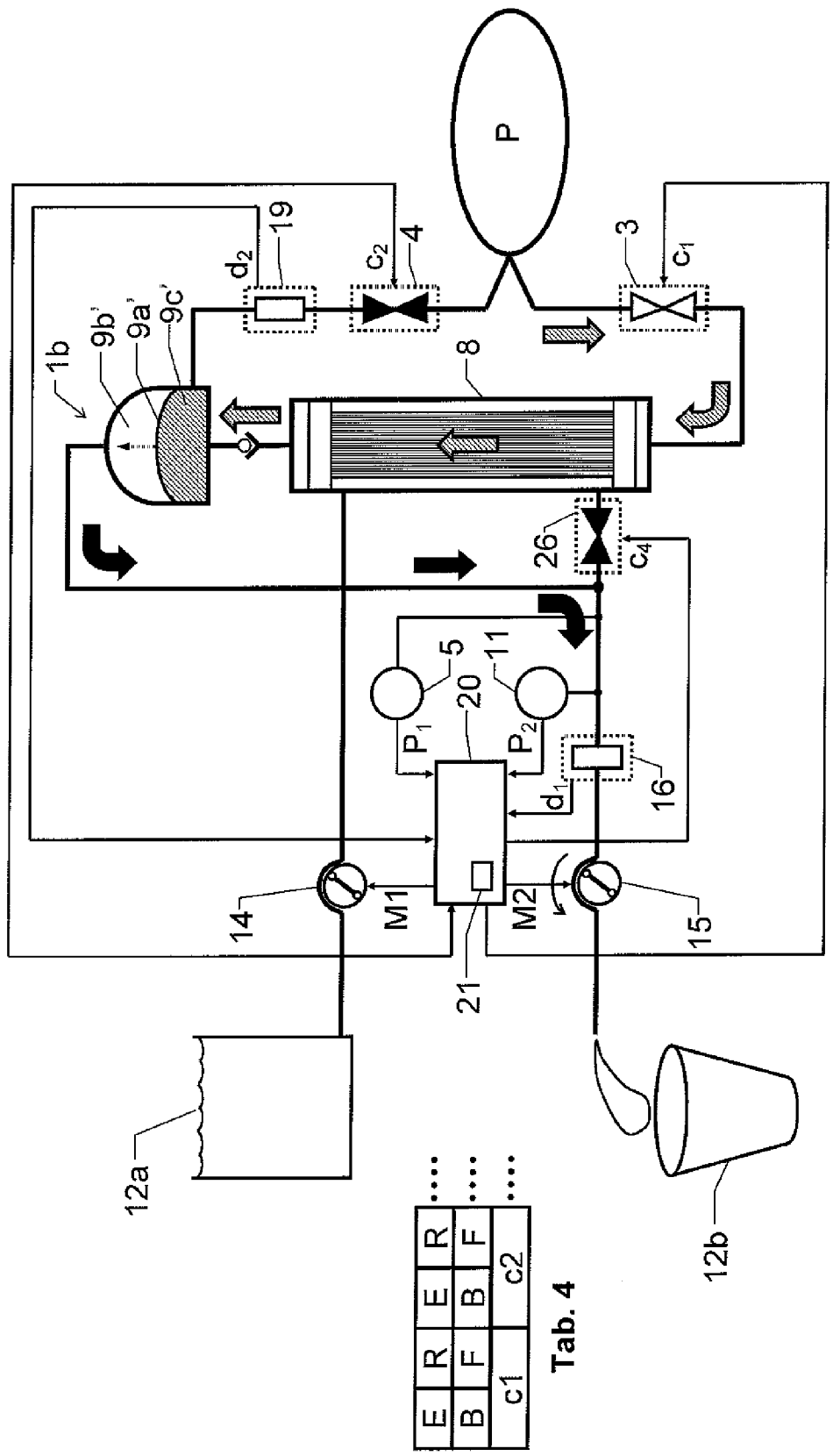
FIGS. 4a-b show block diagrams over a blood treatment apparatus according to a fourth embodiment of the invention during a first and a second phase respectively of a cyclic treatment process.
Figure 4B:
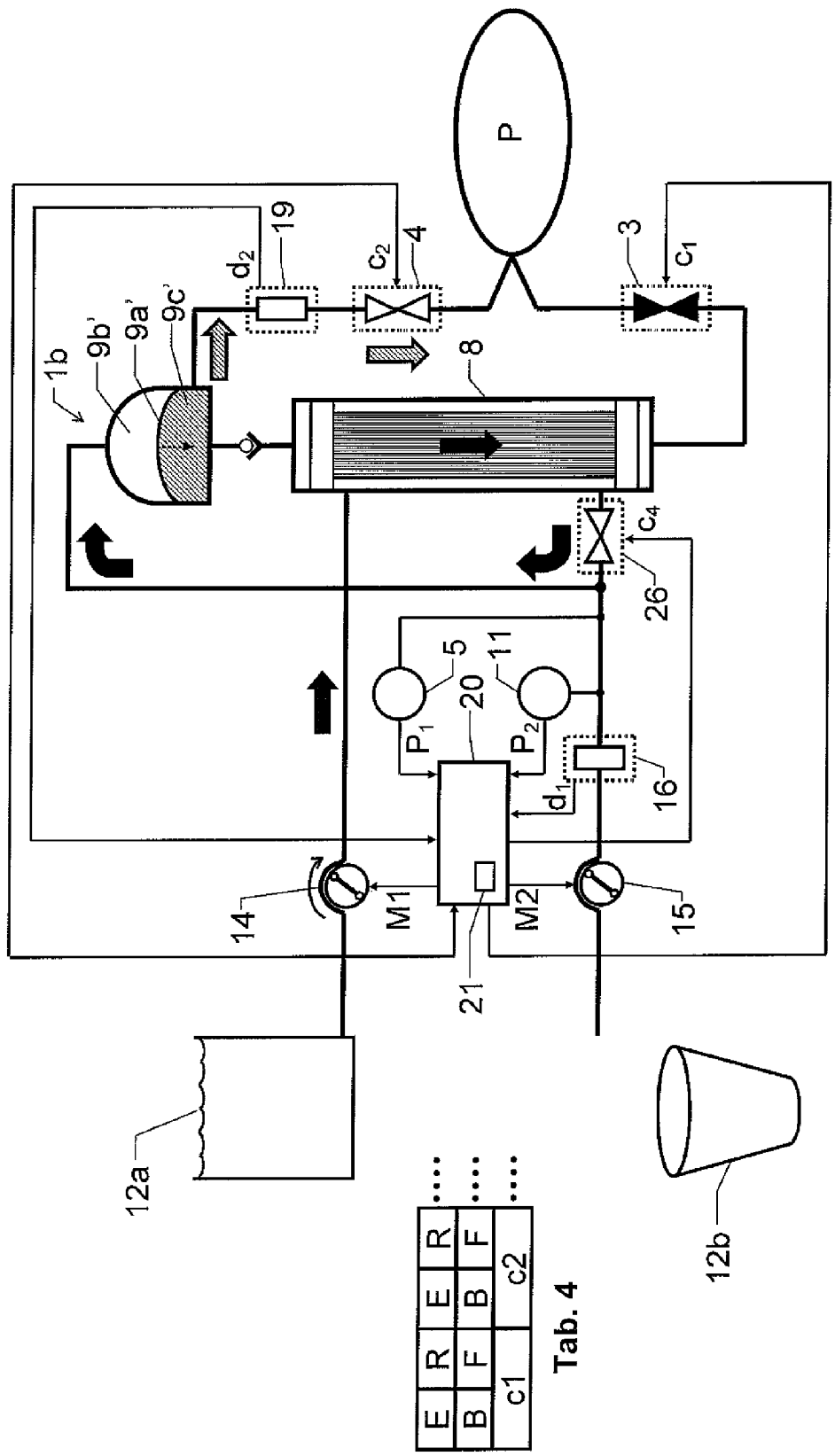

FIGS. 4a and 4b each shows a block diagram over a blood treatment apparatus according to a fourth embodiment of the invention. All units and components having reference signs which also occur in FIGS. 1a through 3b designate the same units and components as those described above with reference to these Figures.

The fourth embodiment differs from the second embodiment of the invention in that a blood pump 1b is arranged on the blood outlet from the blood treatment unit 8 (instead of on the blood inlet). A result of this design is that, analogous to the first embodiment, alternating flows of blood and blood treatment fluid through the blood treatment unit 8 may be accomplished, as illustrated in Table 4.

Figure 5A:
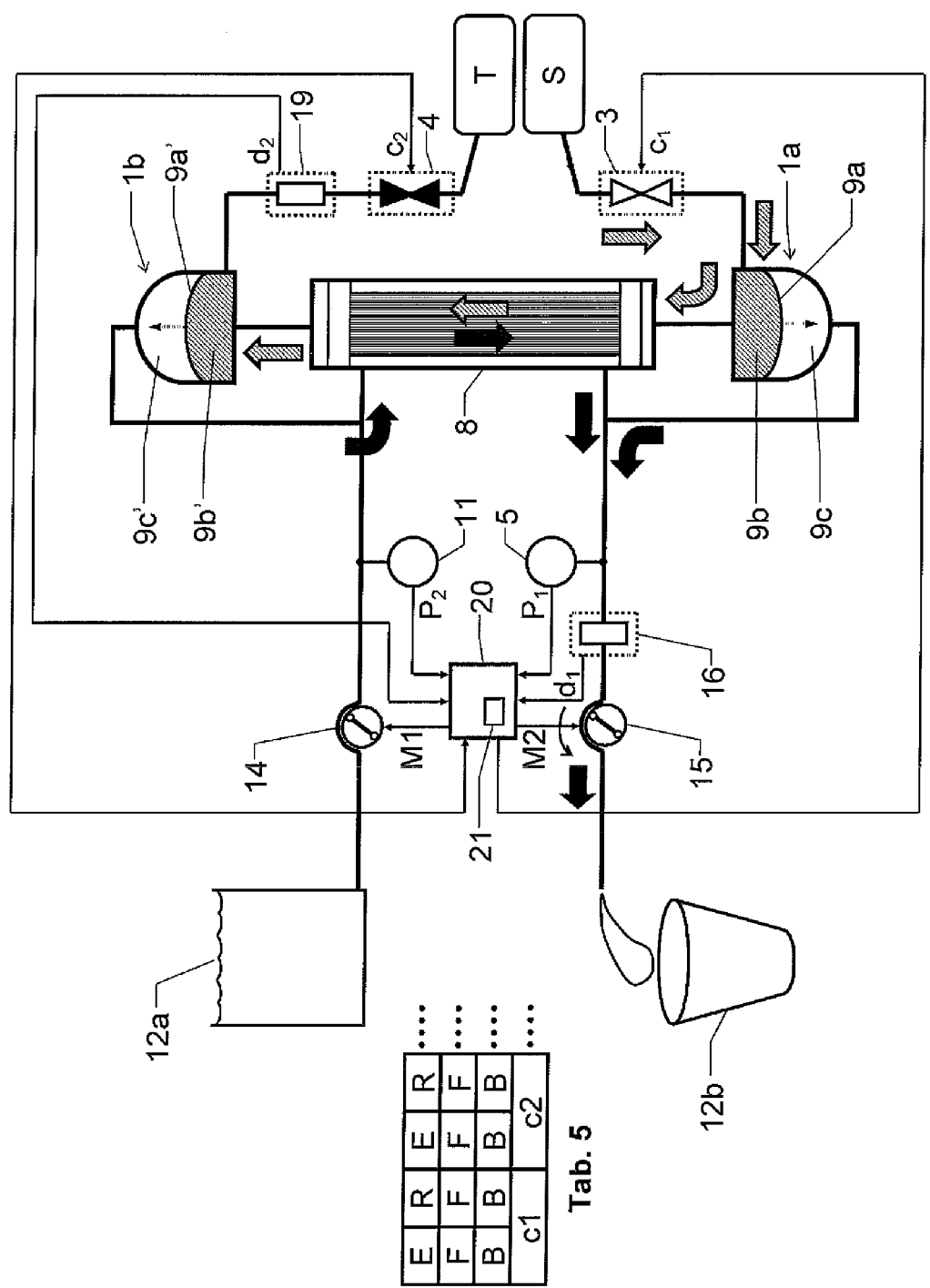
FIGS. 5a-b show block diagrams over a blood treatment apparatus according to a fifth embodiment of the invention during a first and a second phase respectively of a cyclic treatment process.
Figure 5B:
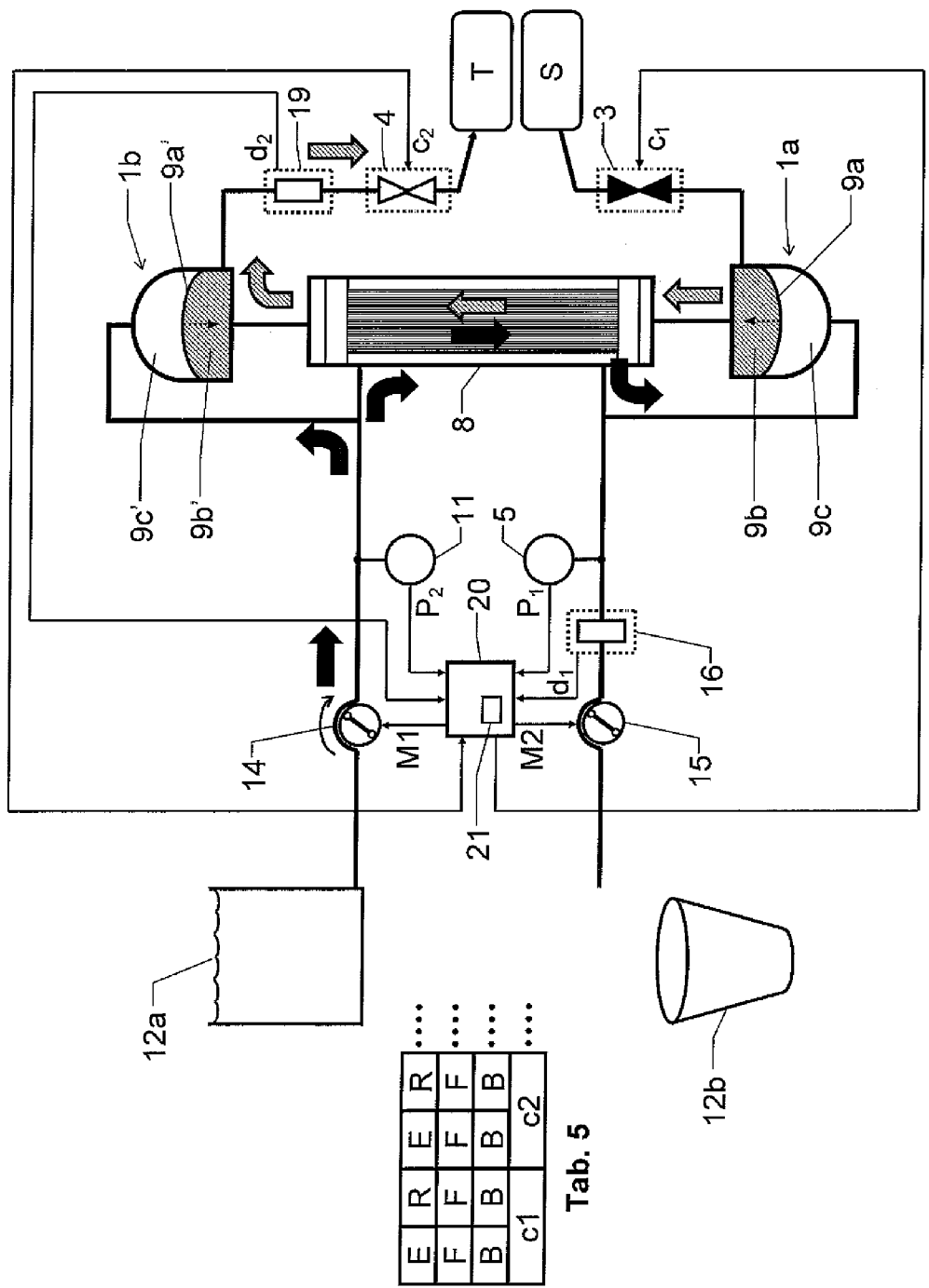

FIGS. 5a and 5b each shows a block diagram over a blood treatment apparatus according to a fifth embodiment of the invention during first and second phases respectively of a cyclic process. Again, all units and components having reference signs which also occur in FIGS. 1a through 4b designate the same units and components as those described above with reference to these Figures. To underline that fact that, according to the invention, the process of blood extraction and blood delivery need not involve a patient, FIGS. 5a and 5b illustrate a general blood source S and a general target vessel T. For example, a respective blood bag may represent the blood source S and the target vessel T. Of course, alternatively, one of these entities S and T may be represented by a patient.

The most significant difference between this embodiment and the embodiments discussed above with reference to FIGS. 1a through 4b is that here the apparatus includes two blood pumps 1a and 1b respectively. Such a double-pump design is advantageous because it allows non-stop flows of blood and blood treatment fluid through the blood treatment unit 8. I.e. blood and blood treatment fluid are passed through the blood treatment unit 8 both during the blood extraction phase E and the blood return phase R, as illustrated in Table 5. Naturally, this is beneficial from an efficiency point-of-view. To enable appropriate operation of this apparatus, the first pressure measuring means 5 is arranged on the fluid conduit which is configured to discharge used blood treatment fluid from the apparatus and thus register the first pressure parameter $P_1$; and the second pressure measuring means 11 is arranged on the fluid conduit which is configured to receive fresh blood treatment fluid from the fluid container 12a and thus register the second pressure parameter $P_2$.

Specifically, the first blood pump 1a has a first blood inlet, a first blood outlet and a first working fluid port. Correspondingly, the second blood pump 1b has a second blood inlet, a second blood outlet and a second working fluid port. Another difference between this embodiment and the embodiments discussed with reference to FIGS. 1a through 4b is that the patient P is exchanged with a blood source S (e.g. a bag containing blood to be treated) and a target vessel T (e.g. a bag configured to hold treated blood).

During the first phase (the blood extraction phase E) of the cyclic process c1, c2 etc., the first blood inlet is configured to receive untreated blood from the blood source S into the first blood pump's 1a first accumulation container 9b, the first blood outlet is configured to discharge the untreated blood from the first blood pump's 1a first accumulation container 9b into the blood treatment unit 8, and the first working fluid port is configured to discharge used blood treatment fluid from the first blood pump's 1a second accumulation container 9c to the fluid outlet conduit. During the blood extraction phase E, the second blood inlet of the second blood pump 1b is also configured to receive treated blood from the blood treatment unit 8 into the second blood pump's 1b first accumulation container 9b', and the second working fluid port is configured to discharge fresh blood treatment fluid from the second blood pump's 1b second accumulation container 9c' into the blood treatment unit 8.

During the second phase (the blood return phase R) of the cyclic process c1, c2 etc., the first blood outlet of the first blood pump 1a is likewise configured to discharge the untreated blood from the first blood pump's 1a first accumulation container 9b into the blood treatment unit 8, and the first working fluid port is configured to receive used blood treatment fluid from the blood treatment unit 8 into the first blood pump's 1a second accumulation container 9c. Moreover, the second blood inlet of the second blood pump 1b is configured to receive treated blood from the blood treatment unit 8 into the second blood pump's 1b first accumulation container 9b', and the second working fluid port is configured to receive fresh blood treatment fluid from the fluid inlet conduit into the second blood pump's 1b second accumulation container 9c'.

Analogous to the earlier described embodiments of the invention, the blood treatment unit 8 includes inlets and outlets for blood treatment fluid and blood respectively. Particularly, a fluid inlet of the unit 8 is configured to receive fresh blood treatment fluid from a fluid container 12a via the first fluid pump 14, and a fluid outlet of the unit 8 is configured to discharge used blood treatment fluid to a fluid outlet conduit, e.g. for disposal in a waste fluid container 12b, via the second fluid pump 15. Moreover, a blood inlet of the unit 8 is configured to receive untreated blood from the first accumulation container 9b of the first blood pump 1a, and a blood outlet of the unit 8 is configured to discharge treated blood into the first accumulation container 9b' of the second blood pump 1b.

Analogous to the other embodiments of the invention, the control unit 20 uses the first and second pressure parameters $P_1$ and $P_2$ to determine appropriate transitions between the first and second phases, i.e. the blood extraction phase E and the blood return phase R respectively.

Figure 6A:
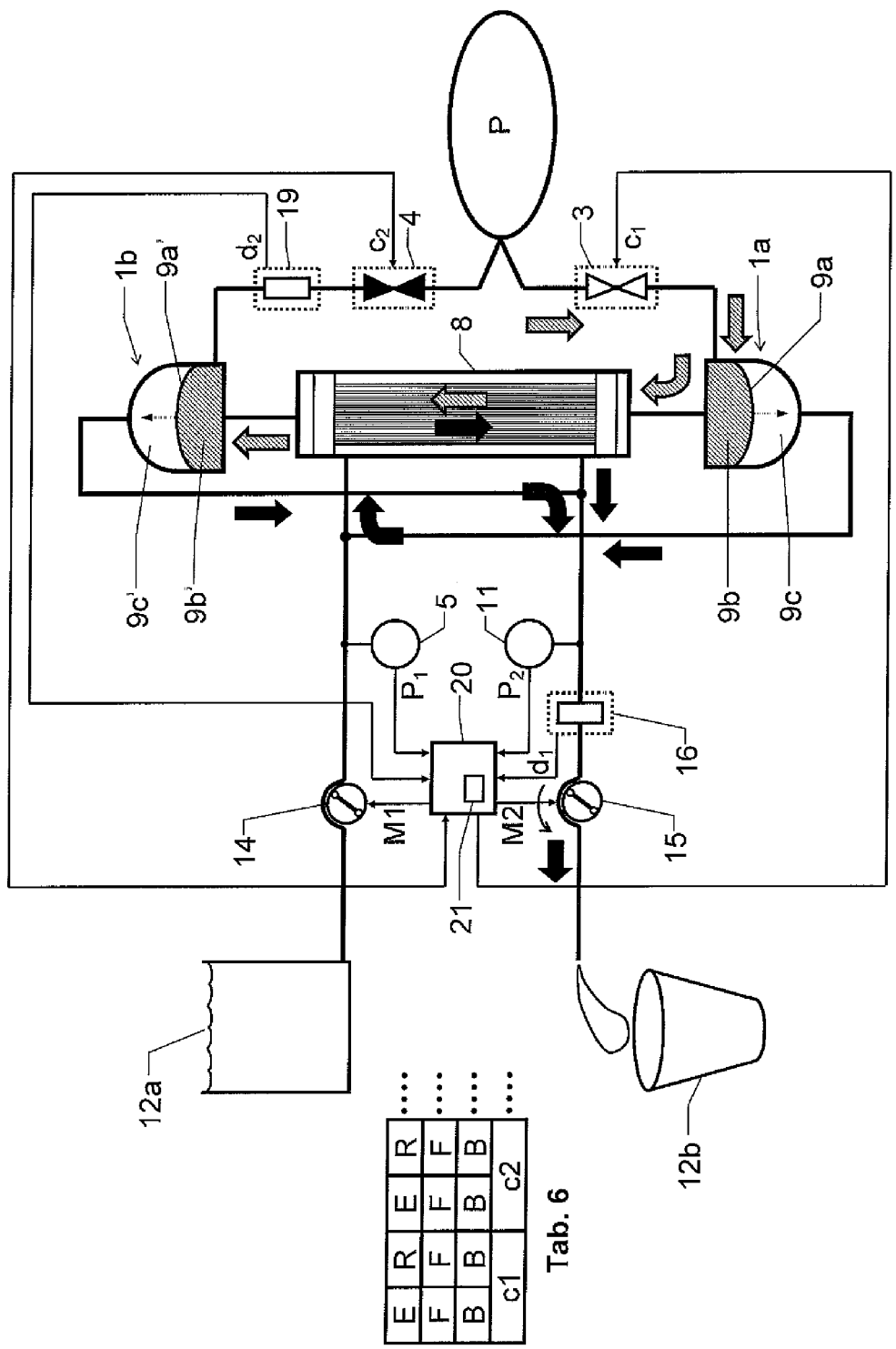
FIGS. 6a-b show block diagrams over a blood treatment apparatus according to a sixth embodiment of the invention during a first and a second phase respectively of a cyclic treatment process.
Figure 6B:
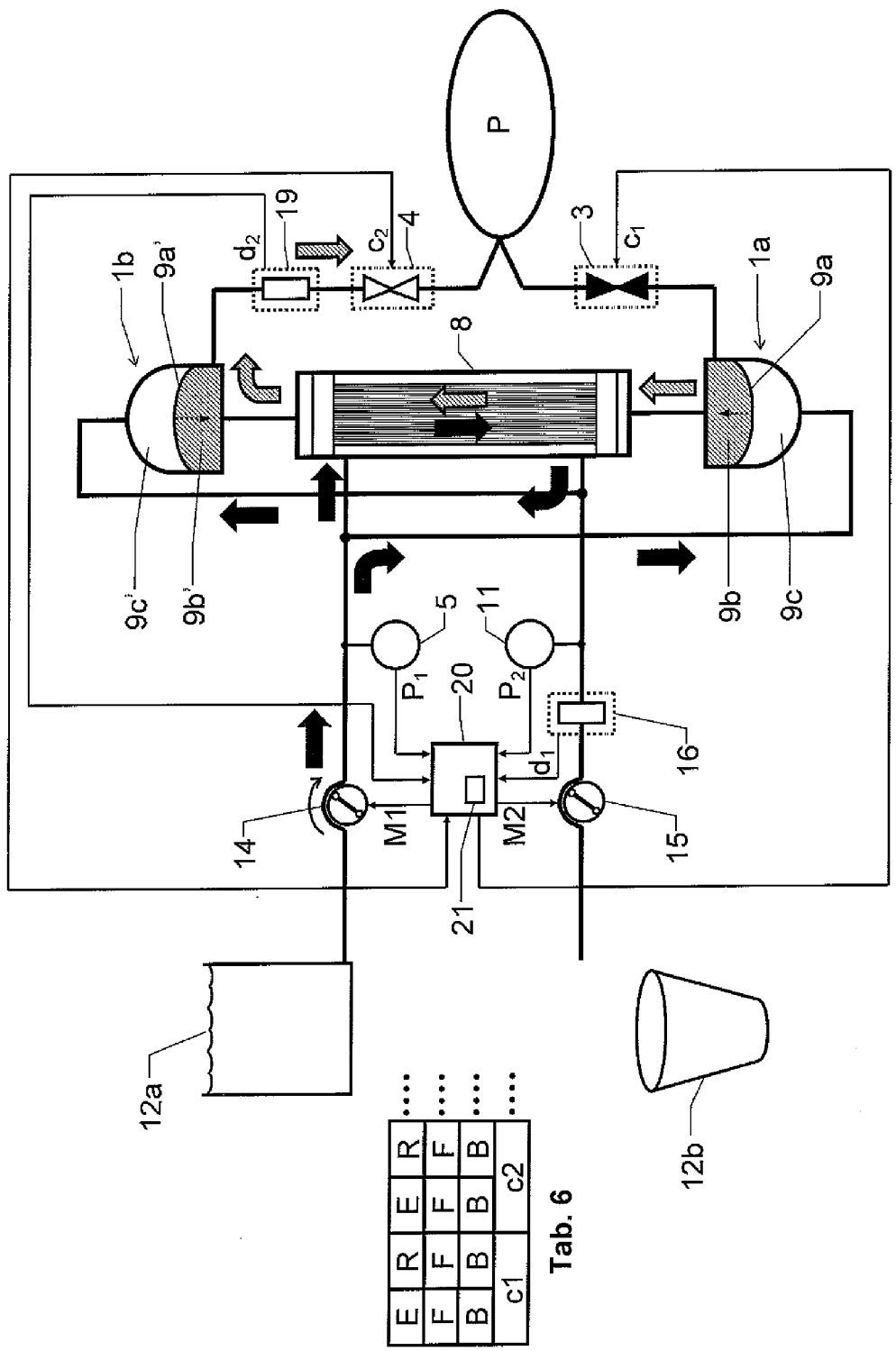

FIGS. 6a and 6b each shows a block diagram over a blood treatment apparatus according to a sixth embodiment of the invention. Once more, all units and components having reference signs which also occur in FIGS. 1a through 5b designate the same units and components as those described above with reference to these Figures.

The key difference between the sixth embodiment shown in FIGS. 6a and 6b, and the fifth embodiment shown in FIGS. 5a and 5b is that in the sixth embodiment, the inlet and outlet conduits for feeding blood treatment fluid into and out from the blood treatment unit 8 respectively are shifted relative to the blood pumps 1a and 1b. As a result, it is a more straightforward task to synchronize the operation of the blood pumps 1a and 1b. By synchronous we here mean that the flexible members 9a and 9a' of the first and second blood pumps 1a and 1b reach their respective end positions simultaneously.

Another effect of said shift is that the first pressure measuring means 5 is configured to register the first pressure parameter $P_1$ on the inlet fluid conduit located downstream of the first fluid pump 14, and conversely, the second pressure measuring means 11 is configured to register the second pressure parameter $P_2$ on the outlet fluid conduit upstream of the second fluid pump 15.

Figure 7:
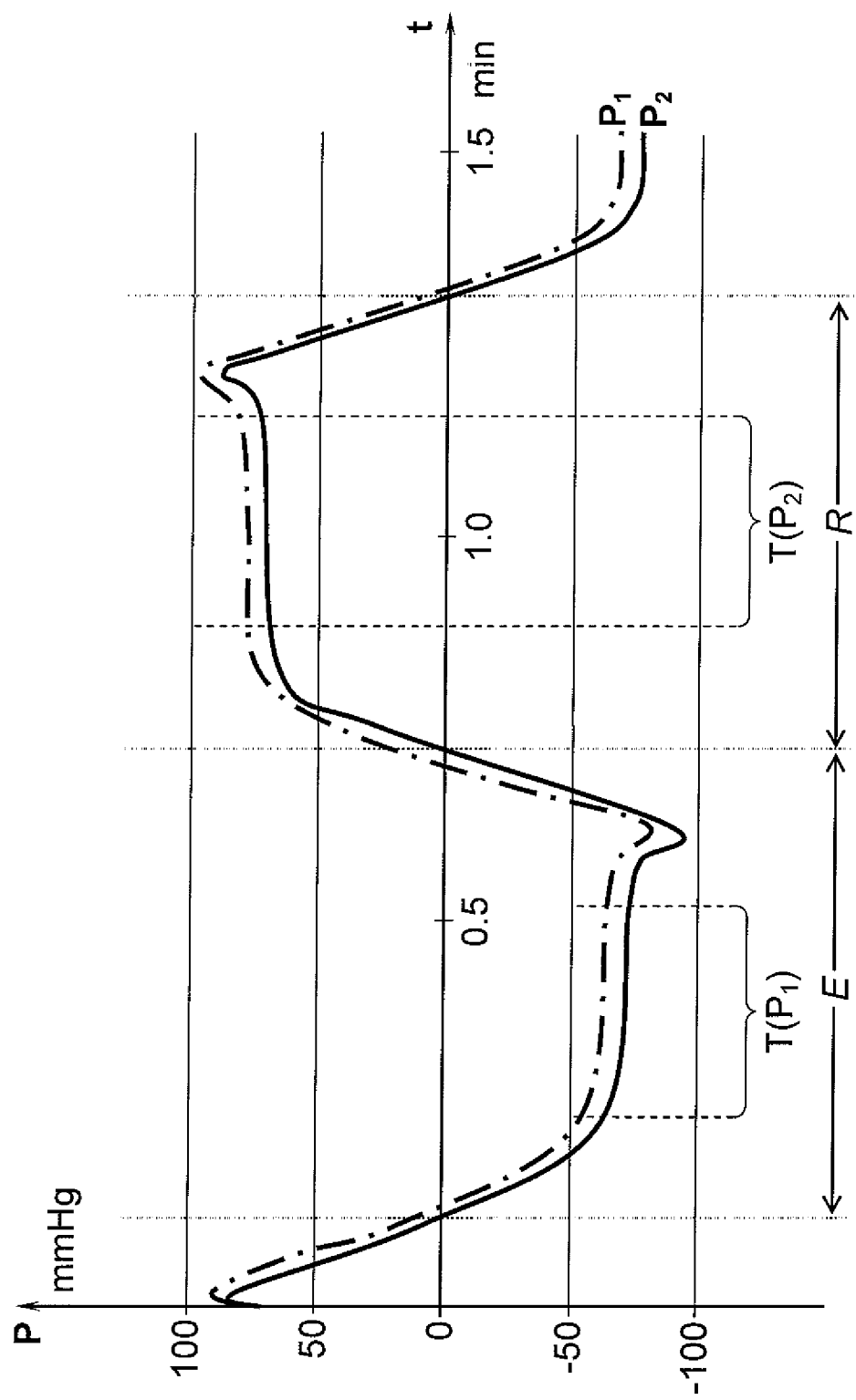
FIG. 7 shows a graph exemplifying pressure relationships of the blood treatment apparatus according to the sixth embodiment of the invention.

FIG. 7 shows a graph, which exemplifies how the first and second pressure parameters $P_1$ and $P_2$ may vary as functions of time t in the blood treatment apparatus according to the above-described sixth embodiment of the invention. The vertical axis represents the pressure P in mmHg, and the time t in minutes is shown along the horizontal axis. As can be seen, one cycle is here approximately 1 minute and 20 seconds long, and the pressures vary between around +95 mmHg and around −95 mmHg.

The pressure parameters essentially follow one another throughout the cyclic procedure; however the first parameter $P_1$ (measured on the inlet fluid conduit) is generally slightly above the second parameter $P_2$ (measured on the outlet fluid conduit). Optionally, the control unit registers the parameters during relatively stable phases of the procedure. This means that the first parameter $P_1$ may be registered during a first pressure measurement window $T(P_1)$ in the blood extraction phase E, and the second parameter $P_2$ may be registered during a second pressure measurement window $T(P_2)$ in the blood return phase R. Optionally, the first parameter $P_1$ registered in the first pressure measurement window $T(P_1)$ monitors that incoming blood is received as expected (designated by a predetermined $P_1$-interval), and the second parameter $P_2$ registered in the second pressure measurement window $T(P_2)$ monitors the output of treated blood (designated by a predetermined $P_2$-interval). Hence, the second parameter $P_2$ may cause an alarm if the needle has been dislodged, or if the conduit thereto is jammed.

Figure 8:
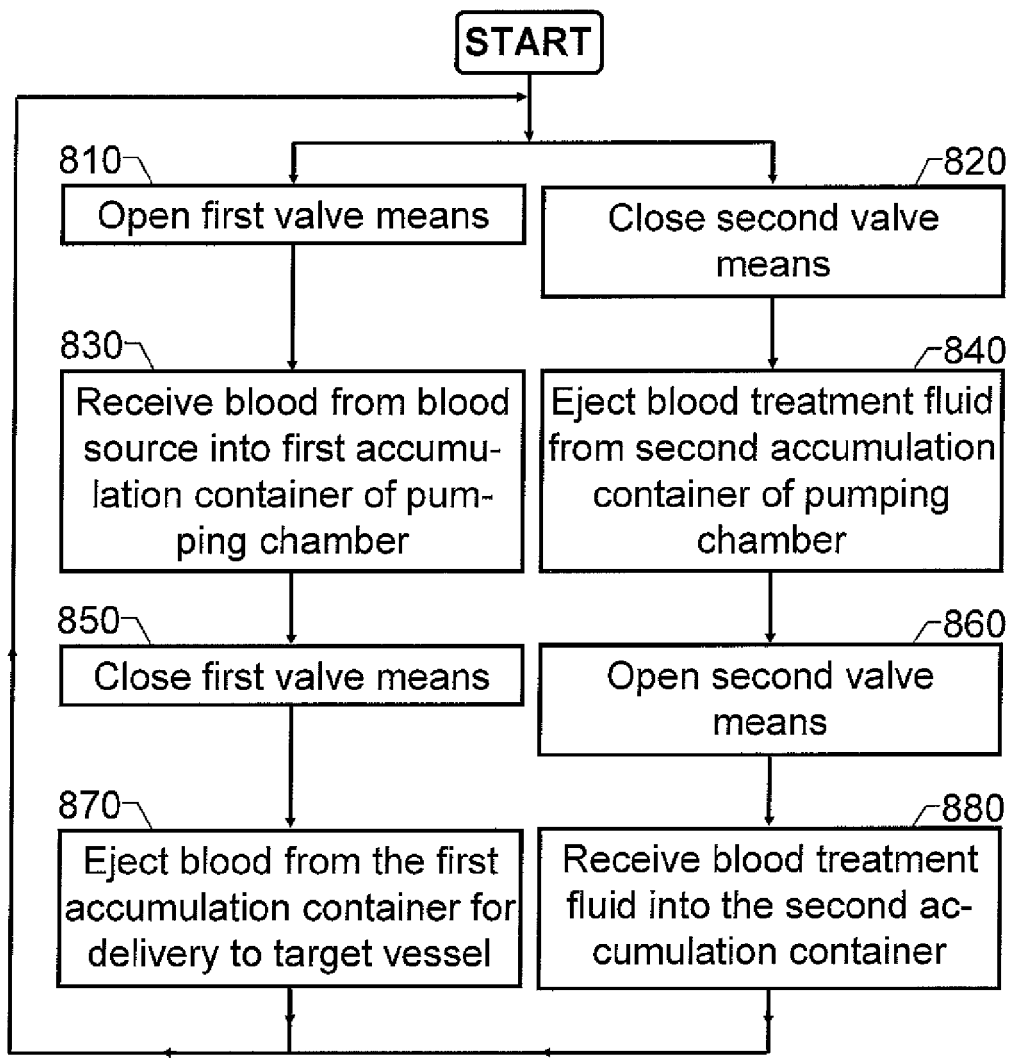
FIG. 8 illustrates, by means of a flow diagram, a general method of operating a blood treatment apparatus according to the invention; and Tables 1-6 illustrate blood extraction and blood return phases relative to when blood treatment fluid respective blood is passed through the blood treatment unit in the different embodiments of the invention.

To sum up, we will now describe the proposed method of operating a blood treatment apparatus, as exemplified by the above-described embodiments, with reference to the flow diagram of FIG. 8. Here, we presume that the apparatus includes a blood treatment unit, at least one fluid pump and at least one blood pump. The pumps are configured to pass blood and blood treatment fluid through the blood treatment unit. Moreover, the pumps are configured to extract untreated blood from a blood source (e.g. a blood bag or a patient), and deliver treated blood to a target vessel (e.g. another blood bag, or the patient from which the blood was extracted). According to the invention, each of the at least one blood pump further includes a pumping chamber and a flexible member separating the pumping chamber into a first accumulation container and a second accumulation container. The flexible member is movable within the pumping chamber, so as to vary a volume relationship between the first and second accumulation containers and thus pump blood from the first accumulation container.

A first phase of the treatment procedure is initiated with a step 810, which opens a first valve means. As a result, blood extracted from the blood source can enter the apparatus. In parallel with step 810, a step 820 closes a second valve means controlling the blood flow from the apparatus back to the target vessel. A step 830 subsequent to step 810 receives the extracted blood in a first accumulation container of a blood pump. Depending on the specific design of the apparatus, the extracted blood either enters directly from the blood source into the first accumulation container (i.e. as untreated), or the blood comes via the blood treatment unit (i.e. after having been treated). In parallel with step 830, a step 840 ejects blood treatment fluid from a second accumulation container of the blood pump. Depending on the apparatus design, the blood treatment fluid in the second accumulation container may either be fresh (i.e. the fluid has not yet passed through the blood treatment unit, however will do so after having been ejected from the second accumulation container), or the blood treatment fluid is used (i.e. the fluid has already passed through the blood treatment unit). If the blood treatment fluid is fresh, it is ejected for further passage through the blood treatment unit. If however, the blood treatment fluid is used, it is ejected for discarding.

Thereafter, a second phase follows. Here, a step 850 closes the first valve means. In parallel with step 850, a step 860 opens the second valve means. Subsequently, a step 870 ejects blood from the first accumulation container of the blood pump for delivery to the target vessel. Again, depending on the apparatus design, the ejected blood may either pass through blood treatment unit, or be fed directly to the target vessel. As discussed above, depending on the design of the apparatus, an additional blood pump may assist in this process. In parallel with step 870, a step 880 receives blood treatment fluid into the second accumulation container. Once more, depending on the design of the apparatus, the received blood treatment fluid may either be fresh (i.e. originate directly from a fluid compartment), or be used (i.e. arrive to the second accumulation container via the blood treatment unit). Then, the procedure loops back to steps 810 and 820 again for completion of another cycle.

All of the steps, as well as any sub-sequence of steps, described with reference to FIG. 8, above may be controlled by means of a programmed computer apparatus. Moreover, although the embodiments of the invention described above with reference to the drawings comprise computer apparatus and processes performed in computer apparatus, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the procedure according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc), an EPROM (Erasable Programmable Read-Only Memory), an EEPROM (Electrically Erasable Programmable Read-Only Memory), or a magnetic recording medium, for example a floppy disc or a hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant procedures.

In this specification, the wording that: "a fluid pump is arranged in/on a conduit" shall be understood to encompass all arrangements wherein the pump is configured to operate on a fluid passing through the conduit. I.e. the pump in question need not actually be included in the conduit. For example the pump may be a hose pump which is configured to manipulate the exterior of a fluid conduit.

The term "comprises/comprising" when used in this specification is taken to specify the presence of stated features, integers, steps or components. However, the term does not preclude the presence or addition of one or more additional features, integers, steps or components or groups thereof.

The reference to any prior art in this specification is not, and should not be taken as, an acknowledgment or any suggestion that the referenced prior art forms part of the common general knowledge in Australia, or in any other country.

The invention is not restricted to the described embodiments in the figures, but may be varied freely within the scope of the claims.

The invention claimed is:

1. A blood treatment apparatus, comprising:
    a blood treatment unit,
    at least one fluid pump configured to pass a blood treatment fluid through the blood treatment unit, and
    at least one blood pump configured to extract untreated blood from a blood source, pass extracted blood through the blood treatment unit and deliver treated blood to a target vessel, wherein the at least one blood pump comprises a pumping chamber and a flexible impermeable member separating the pumping chamber into a first accumulation container and a second accumulation container, the flexible impermeable member being movable within the pumping chamber so as to vary a volume relationship between the first and second accumulation containers, the second accumulation container being configured to receive an amount of the blood treatment fluid to act on the flexible impermeable member and thus pump blood from the first accumulation container,
    a least one pressure measuring device arranged to sense a pressure of the blood treatment fluid in a blood treatment fluid passage including the second accumulation container and at least one conduit for the blood treatment fluid, wherein the at least one pressure measuring device is arranged to register a pressure parameter representing a pressure level of the blood based on a pressure measurement of the blood treatment fluid.

2. The blood treatment apparatus according to claim 1, wherein the at least one pressure measuring device includes at least a first pressure measuring device and a second pressure measuring device, said first pressure measuring device being configured to register a first pressure parameter representing a first pressure level of the untreated blood extracted from the blood source and said second pressure measuring device being configured to register a second pressure parameter representing a second pressure level of the treated blood delivered to the target vessel.

3. The blood treatment apparatus according to claim 2, further comprising: a first blood valve configured to control the extraction of untreated blood from the blood source, and a second blood valve configured to control the delivery of treated blood to the target vessel.

4. The blood treatment apparatus according to claim 1, wherein the blood treatment fluid passage further comprises a fluid inlet conduit configured to receive fresh blood treatment fluid into the apparatus, and a fluid outlet conduit configured to discharge used blood treatment fluid from the apparatus.

5. The blood treatment apparatus according to claim 4, wherein the at least one blood pump is a single blood pump, the apparatus further comprises a fluid valve coupled to the blood treatment passage and arranged to direct a flow of blood treatment fluid through the blood pump, and a control unit configured to control the fluid valve to open and close repeatedly.

6. The blood treatment apparatus according to claim 5, wherein the fluid valve is arranged on a fluid inlet of blood treatment passage which feeds fresh blood treatment fluid into the blood treatment unit, and the control unit is configured to control the fluid valve to:
    direct a flow of fresh blood treatment fluid from the second accumulation container of the blood pump to the blood treatment unit during a first phase of a cyclic process, and
    direct a flow of fresh blood treatment fluid from the fluid container to the second accumulation container of the blood pump during a second phase of the cyclic process.

7. The blood treatment apparatus according to claim 5, wherein the fluid valve is arranged on the fluid outlet of the blood treatment passage and the fluid outlet discharges used blood treatment fluid from the apparatus, and the control unit is configured to control the fluid valve to:

direct a flow of used blood treatment fluid from the second accumulation container of the blood pump out through the discharge outlet during a first phase of a cyclic process, and direct a flow of used blood treatment fluid from the blood treatment unit into the second accumulation container of the blood pump during a second phase of the cyclic process.

8. The blood treatment apparatus according to claim 4, wherein the at least one fluid pump includes:
a first fluid pump arranged on the fluid inlet conduit included in the blood treatment fluid passage, the first fluid pump being configured to feed fresh blood treatment fluid into the blood treatment fluid passage, and
a second fluid pump arranged on the fluid outlet conduit, the second fluid pump being configured to discharge used blood treatment fluid through the blood treatment passage and from the apparatus.

9. The blood treatment apparatus according to claim 8, wherein the control unit is configured to control the operation of the first and second fluid pumps in response to first and second pressure parameters.

10. A blood treatment apparatus comprising:
a blood treatment unit,
at least one fluid pump configured to pass a blood treatment fluid through the blood treatment unit,
a first blood pump configured to extract untreated blood from a blood source and pass the untreated blood to the blood treatment unit,
a second blood pump configured to pass extracted blood from the blood treatment unit and deliver treated blood to a target vessel,
wherein the first and second blood pumps each comprises a pumping chamber and a flexible impermeable member separating the pumping chamber into a first accumulation container and a second accumulation container, the flexible impermeable member being movable within the pumping chamber to vary a volume relationship between the first and second accumulation containers, the second accumulation container being configured to receive a blood treatment fluid to act on the flexible impermeable member to pump blood from the first accumulation container, wherein:
the first blood pump is configured to:
receive untreated blood from the blood source into the first accumulation container of the first blood pump and discharge used blood treatment fluid from the second accumulation container of the first blood pump during a first phase of a cyclic process, and
receive used blood treatment fluid from the blood treatment unit in the second accumulation container of the first blood pump and eject untreated blood from the first accumulation container of the first blood pump into the blood treatment unit during a second phase of the cyclic process, and
the second blood pump is configured to:
eject fresh blood treatment fluid into the blood treatment unit from the second accumulation container of the second blood pump and receive treated blood from the blood treatment unit in the first accumulation container of the second blood pump during the first phase of the cyclic process, and
eject treated blood from the first accumulation container of the second blood pump to the target vessel and receive fresh blood treatment fluid in the second accumulation container of the second blood pump during the second phase of the cyclic process.

11. A blood treatment apparatus comprising:
a blood treatment unit,
at least one fluid pump configured to pass a blood treatment fluid through the blood treatment unit,
a first blood pump configured to extract untreated blood from a blood source and pass the untreated blood to the blood treatment unit,
a second blood pump configured to pass extracted blood from the blood treatment unit and deliver treated blood to a target vessel,
wherein the first and second blood pumps each comprises a pumping chamber and a flexible impermeable member separating the pumping chamber into a first accumulation container and a second accumulation container, the flexible impermeable member being movable within the pumping chamber to vary a volume relationship between the first and second accumulation containers, the second accumulation container being configured to receive a blood treatment fluid to act on the flexible impermeable member to pump blood from the first accumulation container, wherein
the first blood pump is configured to:
receive untreated blood from the blood source into the first accumulation container of the first blood pump and discharge fresh blood treatment fluid from the second accumulation container of the first blood pump during a first phase of a cyclic process, and
receive fresh blood treatment fluid in the second accumulation container of the first blood pump and eject untreated blood from the first accumulation container of the first blood pump into the blood treatment unit during a second phase of the cyclic process, and
the second blood pump is configured to:
eject used blood treatment fluid from the second accumulation container of the second blood pump and receive treated blood from the blood treatment unit in the first accumulation container of the second blood pump during the first phase of the cyclic process, and
eject treated blood from the first accumulation container of the second blood pump to the target vessel and receive used blood treatment fluid from the blood treatment unit in the second accumulation container of the second blood pump during the second phase of the cyclic process.

12. A method of treating blood in a blood treatment apparatus including a blood treatment unit, at least one fluid pump configured to pass a blood treatment fluid through the blood treatment unit, and at least one blood pump configured to extract untreated blood from a blood source, pass extracted blood through the blood treatment unit and deliver treated blood to a target vessel, the at least one blood pump further including a pumping chamber and a flexible impermeable member separating the pumping chamber into a first accumulation container and a second accumulation container, the flexible impermeable member being movable within the pumping chamber to vary a volume relationship between the first and second accumulation containers to pump blood through the first accumulation container, the method comprises:
during a first phase: receiving blood from the blood source in the first accumulation container, and ejecting blood treatment fluid from the second accumulation container,
during a second phase subsequent to the first phase: ejecting blood from the first accumulation container for delivery to the target vessel, and receiving blood treatment fluid into the second accumulation container, and determining a pressure level of the blood during at least one of the first and second phases by measuring a pressure of the blood treatment fluid during the at least one of the first and second phases.

13. The method according to claim 12, wherein the determining of the pressure level includes:

registering a first pressure parameter representing a first pressure level of the untreated blood extracted from the blood source, the first pressure parameter being registered on the blood treatment fluid passage, and registering a second pressure parameter representing a second pressure level of the treated blood delivered to the target vessel, the second pressure parameter being registered on the blood treatment fluid passage.

14. The method according to claim 13, comprising: controlling the extraction of untreated blood from the blood source by a first blood valve, and controlling the delivery of treated blood to the target vessel by means of a second blood valve.

15. The method according to claim 12, comprising:

receiving fresh blood treatment fluid into the apparatus via a fluid inlet conduit included in the blood treatment fluid passage, and discharging used blood treatment fluid from the apparatus via a fluid outlet conduit of the blood treatment fluid passage.

16. The method according to claim 15, wherein at least one blood pump is a single blood pump and the apparatus further includes a fluid valve arranged to direct a flow of blood treatment fluid through the single blood pump, and the method further comprises controlling the fluid valve to open and close repeatedly.

17. The method according to claim 16, wherein the fluid valve is arranged on a fluid inlet of the blood treatment fluid passage, and the fluid inlet receives fresh blood treatment fluid into the blood treatment unit, and the method comprises controlling the fluid valve to:

direct a flow of fresh blood treatment fluid from the second accumulation container of the single blood pump to the blood treatment unit during a first phase of a cyclic process, and direct a flow of fresh blood treatment fluid from the fluid container to the second accumulation container of the single blood pump during a second phase of the cyclic process.

18. The method according to claim 16, wherein the fluid valve is arranged on the fluid outlet for discharging used blood treatment fluid from the apparatus, and the method comprises controlling the fluid valve to: direct a flow of used blood treatment fluid from the second accumulation container of the single blood pump out through the discharge outlet during a first phase of a cyclic process, and direct a flow of used blood treatment fluid from the blood treatment unit into the second accumulation container of the single blood pump during a second phase of the cyclic process.

19. The method according to claim 16, wherein the at least one fluid pump includes a first fluid pump arranged on the fluid inlet conduit and a second fluid pump arranged on the fluid outlet conduit, and the method further comprises:

controlling the first fluid pump to feed fresh blood treatment fluid into the apparatus, and controlling the second fluid pump to discharge used blood treatment fluid from the apparatus.

20. The method according to claim 19, further comprising controlling the operation of the first and second fluid pumps in response to the first and second pressure parameters.

21. A computer program loadable into the non-transitory memory of a computer, comprising software for controlling the steps of claim 12 or 16 when said program is run on the computer.

22. A non-transitory computer readable medium, having a program recorded thereon, where the program is to make a computer control the steps of claim 12 or 16 when the program is loaded into the computer.

23. A method of treating blood in a blood treatment apparatus including a blood treatment unit, at least one fluid pump configured to pass a blood treatment fluid through the blood treatment unit, a first blood pump configured to extract untreated blood from a blood source and pass the untreated blood into the blood treatment apparatus, and a second blood pump configured to pass treated blood from the blood treatment unit to a target vessel, wherein the first and second blood pumps each include a pumping chamber and a flexible impermeable member separating the pumping chamber into a first accumulation container and a second accumulation container, the flexible impermeable member being movable within the pumping chamber to vary a volume relationship between the first and second accumulation containers and thus pump blood that is being passed through the first accumulation container, wherein the method comprises:

during a first phase of a cyclic process: receiving untreated blood from the blood source into the first accumulation container of the first blood pump, discharging used blood treatment fluid from the second accumulation container of the first blood pump, receiving treated blood from the blood treatment unit in the first accumulation container of the second blood pump, and ejecting fresh blood treatment fluid into the blood treatment unit from the second accumulation container of the second blood pump, and during a second phase of the cyclic process: receiving used blood treatment fluid from the blood treatment unit in the second accumulation container of the first blood pump ejecting untreated blood from the first accumulation container of the first blood pump into the blood treatment unit, receiving fresh blood treatment fluid in the second accumulation container of the second blood pump, and ejecting treated blood from the first accumulation container of the second blood pump to the target vessel.

24. A method of treating blood in a blood treatment apparatus including a blood treatment unit, at least one fluid pump configured to pass a blood treatment fluid through the blood treatment unit, a first blood pump configured to extract untreated blood from a blood source and pass the untreated blood into the blood treatment apparatus, and a second blood pump configured to pass treated blood from the blood treatment unit to a target vessel, wherein the first and second blood pumps each include a pumping chamber and a flexible impermeable member separating the pumping chamber into a first accumulation container and a second accumulation container, the flexible impermeable member being movable within the pumping chamber to vary a volume relationship between the first and second accumulation containers and thus pump blood that is being passed through the first accumulation container, wherein the method comprises:

during a first phase of a cyclic process: receiving untreated blood from the blood source into the first accumulation container of the first blood pump, ejecting fresh blood treatment fluid from the second accumulation container of the first blood pump into the blood treatment unit, receiving treated blood from the blood treatment unit in the first accumulation container of the second blood pump, and discharging used blood treatment fluid from the second accumulation container of the second blood pump, and during a second phase of the cyclic process: receiving fresh blood treatment fluid in the second accumulation container of the first blood pump, ejecting untreated blood from the first accumulation container of the first blood pump into the blood treatment unit, receiving used blood treatment fluid from the blood treatment unit in the second accumulation container of the second blood pump, and ejecting treated blood from the first accumulation container of the second blood pump to the target vessel.

25. A blood treatment apparatus comprising:

a blood treatment unit configured to treat blood with a blood treatment fluid, wherein the blood treatment unit is in fluid communication with a source of untreated blood and a target vessel for treated blood, and the blood treatment unit is coupled to a treatment fluid conduit in fluid communication with a source of the blood treatment fluid;

at least one treatment fluid pump connectable to the treatment fluid conduit and configured to pump the blood treatment fluid through the treatment fluid conduit, and at least one blood pump connectable to a blood conduit in fluid communication with a source of untreated blood and to a target for treated blood, the at least one blood pump comprises a pumping chamber and a flexible impermeable member separating the pumping chamber into a first accumulation container and a second accumulation container, the flexible impermeable member being movable within the pumping chamber to vary a volume relationship between the first and second accumulation containers, wherein the second accumulation container is connectable to the treatment fluid conduit and configured to receive the blood treatment fluid pumped by the at least one fluid pump to act on the flexible impermeable member to pump blood through the first accumulation container.

26. A method to treat blood in a blood treatment apparatus including a blood treatment unit, at least one treatment fluid pump and at least one blood pump, wherein the blood pump includes a pumping chamber and a flexible impermeable member separating the pumping chamber into a first accumulation container and a second accumulation container, the method comprises:

pumping, with the at least one treatment fluid pump, treatment fluid through the blood treatment unit;

pumping, with the at least one treatment fluid pump, the treatment fluid from the second accumulation chamber which moves the flexible membrane and draws blood from a blood source into in the first accumulation container pumping, with the at least one treatment fluid pump, the treatment fluid into the second accumulation chamber which moves the flexible membrane and discharges blood from the first accumulation container;

moving the blood through the blood treatment unit by either or both the drawing or the discharging of the blood into or from the first accumulation chamber, wherein the blood moving through the blood treatment unit is treated using the treatment fluid moving through the blood treatment unit, and moving treated blood into a target vessel from the blood treatment unit by either or both the drawing or the discharging of the blood into or from the first accumulation chamber.

* * * * *